(12) United States Patent
Hotamisligil et al.

(10) Patent No.: US 10,882,901 B2
(45) Date of Patent: Jan. 5, 2021

(54) METHODS OF TREATING DIABETES BY AN ADIPOCYTE PROTEIN 2 SPECIFIC ANTIBODY

(71) Applicant: President and Fellows of Harvard College, Cambridge, MA (US)

(72) Inventors: Gokhan S. Hotamisligil, Wellesley, MA (US); Haiming Cao, Bethesda, MD (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/851,040

(22) Filed: Dec. 21, 2017

(65) Prior Publication Data
US 2018/0105586 A1 Apr. 19, 2018

Related U.S. Application Data

(63) Continuation of application No. 15/093,508, filed on Apr. 7, 2016, now Pat. No. 9,879,078, which is a continuation of application No. 13/203,880, filed as application No. PCT/US2010/026305 on Mar. 5, 2010, now abandoned.

(60) Provisional application No. 61/299,170, filed on Jan. 28, 2010, provisional application No. 61/209,251, filed on Mar. 5, 2009.

(51) Int. Cl.
*A61K 39/00* (2006.01)
*C07K 16/18* (2006.01)

(52) U.S. Cl.
CPC ........ *C07K 16/18* (2013.01); *A61K 2039/505* (2013.01); *C07K 2317/34* (2013.01); *C07K 2317/76* (2013.01)

(58) Field of Classification Search
CPC .............................. C07K 6/18; C07K 2317/34
See application file for complete search history.

(56) References Cited

U.S. PATENT DOCUMENTS

| | | | |
|---|---|---|---|
| 5,858,366 A | 1/1999 | Sodroski et al. | |
| 5,889,167 A | 3/1999 | Cascieri et al. | |
| 6,548,529 B1 | 4/2003 | Robl et al. | |
| 7,390,824 B1 | 6/2008 | Robl et al. | |
| 8,846,413 B2 | 9/2014 | Ruzicka | |
| 2002/0035064 A1 | 3/2002 | Robl et al. | |
| 2003/0040516 A1 | 2/2003 | Sulsky et al. | |
| 2004/0010119 A1 | 1/2004 | Guo et al. | |
| 2012/0134998 A1 | 5/2012 | Hotamisligil et al. | |
| 2015/0093769 A1 | 4/2015 | Ruzicka | |

FOREIGN PATENT DOCUMENTS

| | | |
|---|---|---|
| DE | 102006034607 | 7/2007 |
| DE | 102006034607 A1 | 7/2007 |
| WO | WO 2000/15229 A1 | 3/2000 |
| WO | WO 2000/047734 A1 | 8/2000 |
| WO | WO 2000/015230 A1 | 3/2000 |
| WO | WO 2003/043624 A1 | 5/2003 |
| WO | WO 2010/057260 A1 | 5/2010 |

OTHER PUBLICATIONS

Chamov and Ashkanazi, TIBTECH 14: 52-60, 1996.*
Rudikoff et al., Proc. Natl. Acad. Sci. 79: 1979-1983, 1982.*
PCT/US2016/030303, Invitation to pay additional fees and, where applicable, protest fee, mailed Sep. 12, 2016.
Banaszak, et al. "Lipid-binding proteins: a family of fatty acid and retinoid transport proteins" Adv. Protein Chem., 1994; 45: 89-151.
Barf, et al. "N-Benzyl-indolo carboxylic acids: Design and synthesis of potent and selective adipocyte fatty-acid binding protein (A-FABP) inhibitors" Bioorganic and Medicinal Chemistry Letters, Mar. 15, 2009; 19(6): 1745-1748.
Baxa, et al. "Human adipocyte lipid-binding protein: purification of the protein and cloning of its complementary DNA" Biochemistry, 1989; 28: 8683-8690.
Blanc, et al. "Exosome release by reticulocytes—An integral part of the red blood cell differentiation system" Blood Cells, Molecules, and Diseases, 2005; 35: 21-26.
Boord, et al. "Adipocyte Fatty Acid-Binding Protein, aP2, Alters Late Atherosclerotic Lesion Formation in Severe Hypercholesterolemia" Arterioscler. Thromb. Vasc. Biol., Oct. 2002; 22(10): 1686-1691.
Cabre, et al. "Fatty acid binding protein 4 is increased in metabolic syndrome and with thiazolidinedione treatment in diabetic patients" Atherosclerosis, 2007; 195: e150-e158.
Cao, et al. "Regulation of Metabolic Responses by Adipocyte/Macrophage Fatty Acid-Binding Proteins in Leptin-Deficient Mice" Diabetes, Jul. 2006; 55: 1915-1922.
Cao, et al. "Identification of a Lipokine, a Lipid Hormone Linking Adipose Tissue to Systemic Metabolism" Cell, Sep. 19, 2008; 134:933-944.
Cao, et al. "Adipocyte lipid chaperone aP2 is a secreted adipokine regulating hepatic glucose production" Cell Metabolism, May 2013; 17(5); 768-778.
Cayman Chemical FABP4 Polyclonal Antibody product sheet (5 pages) downloaded on Sep. 30, 2015.
Distel, et al. "Fatty Acid Regulation of Gene Expression: Transcriptional and Post-Transcriptional Mechanisms" The Journal of Biological Chemistry, Mar. 25, 1992; 267(9): 5937-5941.
Erbay, et al. "Reducing endoplasmic reticulum stress through a macrophage lipid chaperone alleviates atherosclerosis" Nature Medicine, Dec. 2009; 15(12): 1383-1391.

(Continued)

Primary Examiner — Gyan Chandra
(74) Attorney, Agent, or Firm — Knowles Intellectual Property Strategies, LLC

(57) ABSTRACT

A method of reducing a symptom of a clinical disorder characterized by aberrantly elevated circulating aP2 is carried out by administering to a subject an inhibitor of secreted aP2, secretion of aP2, or a serum aP2 blocking agent. For example, glucose intolerance is reduced following administration of such an inhibitor or agent. Exemplary compositions inhibit cellular secretion of aP2 or bind to circulating aP2, thereby reducing the level or activity of aP2 in blood or serum.

5 Claims, 21 Drawing Sheets

Specification includes a Sequence Listing.

(56) References Cited

OTHER PUBLICATIONS

Fu, et al. "Oxidized LDL induces the expression of ALBP/aP2 mRNA and protein in human THP-1 macrophages" Journal of Lipid Research, 2000; 41: 2017-2023.
Furuhashi, et al. "Treatment of diabetes and atherosclerosis by inhibiting fatty-acid-binding protein aP2" Nature, 2007; 447(21): 959-965.
Furuhashi, et al. "Adipocyte/Macrophage Fatty Acid-Binding Proteins Contribute to Metabolic Deterioration Through Actions in Both Macrophages and Adipocytes in Mice" J_ Clin. Invest., Jul. 2008; 118(7):2640-2650.
Gillian, et al. "Structural Basis for Activation of Fatty Acid-binding Protein 4" J. Mol. Biol., 2007; 372:1246-1260.
Girona, et al. "FABP4 Induces Vascular Smooth Muscle Cell Proliferation and Migration through a MAPK—Dependent Pathway" PLoS One, Nov. 2013; 8(11): e81914.
Gorbenko, et al. "Generation and Characterization of Monoclonal Antibodies against FABP4" Hybridoma, 2006; 25(2):86-90.
Hecker, et al. "Heat shock proteins as biomarkers for the rapid detection of brain and spinal cord ischemia: a review and comparison to other methods of detection in thoracic aneurysm repair" Cell Stress and Chaperones, 2011; 16: 119-131.
Hellberg, et al. "X-ray crystallographic analysis of adipocyte fatty acid binding protein (aP2) modified with 4-hydroxy-2-nonenal" Protein Science, 2010; 19: 1480-1489.
Hertzel, et al. "The Mammalian Fatty Acid-binding Protein Multigene Family: Molecular and Genetic Insights into Function" Trends in Endocrinology & Metabolism, 2000; 11(5): 175-180.
Hertzel, et al. "Identification and characterization of a small molecule inhibitor of Fatty Acid binding proteins" Journal of Medicinal Chemistry, Oct. 8, 2009; 52(19): 6024-6031.
Hotamisligil, et al. "Uncoupling of Obesity from Insulin Resistance Through a Targeted Mutation in aP2, the Adipocyte Fatty Acid Binding Protein" Science, Nov. 22, 1996; 274(5291): 1377-1379.
Hunt, et al. "Adipocyte P2 gene: Developmental expression and homology of 5'-flanking sequences among fat cell-specific genes" PNAS, Jun. 1986; 83: 3786-3790.
Hunter-Lavin, et al. "Hsp70 release from peripheral blood mononuclear cells" Biochemical and Biophysical Research Communications, Nov. 12, 2004; 324(2): 511-517.
Kajimura et al. "Regulation of the brown and white fat gene programs through a PRDM16/CtBP transcriptional complex" Genes & Development, 2008; 22: 1397-1409.
Karakas et al. "Serum fatty acid binding protein 4, free fatty acids, and metabolic risk markers" Metabolism Clinical and Experimental, 2009; 58: 1002-1007.
LaLonde, et al. "X-ray Crystallographic Structures of Adipocyte Lipid-Binding Protein Complexed with Palmitate and Hexadecanesulfonic Acid. Properties of Cavity Binding Sites" Biochemistry, 1994; 33: 4885-4895.
Lan, et al. "Small-molecule inhibitors of FABP4/5 ameliorate dyslipidemia but not insulin resistance in mice with diet-induced obesity" Journal of Lipid Research, Apr. 2011; 52(4): 646-656.
Layne et al. "Role of macrophage-expressed adipocyte fatty acid binding protein in the development of accelerated atherosclerosis in hypercholesterolemic mice" The FASEB Journal, Dec. 2001; 15: 2733-2735.
Lehmann, et al. "Discovery of inhibitors of human adipocyte fatty acid-binding protein, a potential type 2 diabetes target" Bioorganic and Medicinal Chemistry Letters, Sep. 6, 2004; 14(17):4445-4448.
Maeda, et al. "Adipocyte/Macrophage Fatty-Acid Bonding Proteins Control Integrated Metabolic Responses in Obesity and Diabetes" Cell Metab., Feb. 2005; 1:107-119.
Makowski, et al. "Lack of Macrophage Fatty-Acid-Binding Protein aP2 Protects Mice Deficient in Apolipoprotein E Against Atherosclerosis" Nat. Med., Jun. 2001; 7(6):699-705.

Makowski et al. "The Fatty Acid-binding Protein, aP2, Coordinates Macrophage Cholesterol Trafficking and Inflammatory Activity" The Journal of Biological Chemistry, Apr. 1, 2005; 280(13): 12888-12895.
Melki et al. "Expression of the adipocyte fatty acid-binding protein streptozotocin-diabetes: effects of insulin deficiency and supplementation" Journal of Lipid Research, 1993; 34: 1527-1534.
Ozcan et al. "Chemical Chaperones Reduce ER Stress and Restore Glucose Homeostasis in a Mouse Model of Type 2 Diabetes" Science, Aug. 25, 2006; 313(5790): 1137-1140.
Ringom, et al. "Substituted benzylamino-6-(trufluoromethyl)pyramidin-4(1H)-ones: a novel class of selective human A-FABP inhibitors" Bioorganic and Medicinal Chemistry Letters, 2004; 14: 4449-4452.
Rosen, et al. "Adipocytes as Regulators of Energy Balance and Glucose Homeostasis" Nature, Dec. 14, 2006; 444:847-853.
Storch, et al. "Structural and functional analysis of fatty acid-binding proteins" Journal of Lipid Research, 2009; 50: S126-S131.
Sulsky, et al. "Potent and selective biphenyl azole inhibitors of adipocyte fatty acid binding protein (aFABP)" Bioorganic and Medicinal Chemistry Letters, Jun. 15, 2007; 17(12): 3511-3515.
Tuncman et al. "A genetic variant at the fatty acid-binding protein aP2 locus reduces the risk for hypertriglyceridemia, type 2 diabetes, and cardiovascular disease" PNAS, May 2, 2006; 103(18): 6970-6975.
Uysal et al. "Improved Glucose and Lipid Metabolism in Genetically Obese Mice Lacking aP2" Endocrinology, 2000; 141: 3388-3396.
van Dongen, et al. "Structure-based screening as applied to human FABP4: a highly efficient alternative to HTS for hit generation" Journal of the American Chemical Society, Oct. 9, 2002; 124(40): 11874-11880.
Vernochet et al. "C/EBPalpha and the Corepressors CtBP1 and CtBP2 Regulate Repression of Select Visceral White Adipose Genes during Induction of the Brown Phenotype in White Adipocytes by Peroxisome Proliferator-Activated Receptor gamma Agonists" Molecular and Cellular Biology, Sep. 2009; 29(17): 4714-4728.
Xu, et al. "The adipocyte lipid-binding protein at 1.6-A resolution. Crystal structures of the apoprotein and with bound saturated and unsaturated fatty acids" Journal of Biological Chemistry, 1993; 268: 7874-7884.
Xu, et al. "Adipocyte Fatty Acid-Binding Protein Is a Plasma Biomarker Closely Associated with Obesity and Metabolic Syndrome" Clinical Chemistry, 2006; 52(3): 405-413.
Xu, et al. "Circulating Adipocyte-Fatty Acid Binding Protein Levels Predict the Development of the Metabolic Syndrome-A 5-Year Prospective Study" Circulation, 2007, 115:1537-1543.
Zhang, et al. "Exosomes" a novel pathway of local and distant intercellular communication that facilitates the growth and metastasis of neoplastic lesions"American Journal of Pathology, Jan. 2014; 184(1)" 28-41.
Braun DA et al., "Interplay of somatic alterations and immune infiltration modulates response to PD-1 blockade in advanced clear cell renal cell carcinoma", Nature Medicine, 2020, 26, 909-918.
International Search Report for PCT/US2010/026305 dated Apr. 10, 2010.
G1 Therapeutics presentation "Hypothesis" Trilaciclib enhances tumor efficacy through immune activation in TNBC (28-04 data), presented Jun. 11, 2020.
Written Opinion of the International Search Authority for PCT/US2010/026305 dated May 9, 2011.
U.S. Pat. No. 9,879,078, B2, U.S. Appl. No. 15/093,508, Hotamisligil et al., filed Jan. 30, 2018.
U.S. Pat. No. 10,160,798, B2, U.S. Appl. No. 15/143,162, Hotamisligil, filed Dec. 25, 2018.
US, 2019/0135888, A1, U.S. Appl. No. 16/228,297, Hotamisligil et al., filed May 9, 2019.
US, 2019/0161536, A1, U.S. Appl. No. 16/197,066, Hotamisligil et al., filed May 30, 2019.
US, 2020/0102380, A1, U.S. Appl. No. 16/708,015, Hotamisligil et al., filed Apr. 2, 2020.

(56) References Cited

OTHER PUBLICATIONS

Brand CL et al., "Immunoneutralization of endogenous glucagon with monoclonal glucagon antibody normalizes hyperglycaemia in moderately streptozotocin-diabetic rats", Diabetologia, 1994, 37(10), 985-993; XP009089852.

Burak Furkan MD et al., "Development of a therapeutic monoclonal antibody that targets secreted fatty acid-binding protein aP2 to treat type 2 diabetes", Sci. Trans. Med., 2015, 7(3), 1-17, XP055558498.

Joyner CJ et al., "Development of a monoclonal antibody to the aP2 protein to identify adipocyte precursors in tumours of adipose differentiation", Pathology Research and Practice, 1999, 195(7), 461-466.

\* cited by examiner

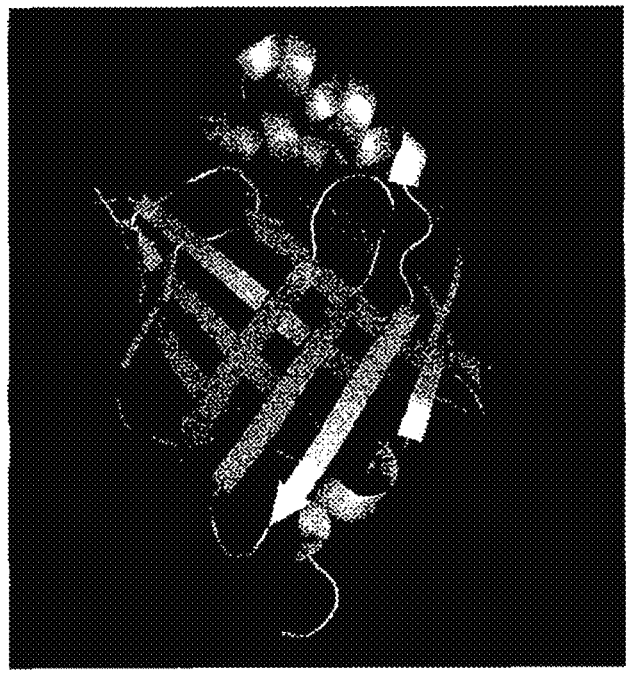

Discontinuous epitopes based on aP2 crystal structure is predicted by a software tool DiscoTope (highlighted on the structure) and residues that constitute these epitopes are labeled in boxes as below.

```
>gi|4557579|ref|NP_001433.1| fatty acid binding protein 4,
adipocyte [Homo sapiens]
MCDAFVGTWKLVSSENFDDYMKEVGVGFATRKVAGMAKPNMIISVNGDVITIKSESTFK
NTEISFILGQEFDEVTADDRKVKSTITLDGGVLVHVQKWDGKSTTIKRKREDDKLVVEC
VMKGVTSTRVYERA    (SEQ ID NO: 3)
```

FIG. 3

Control

Palmitate

FIG. 6A
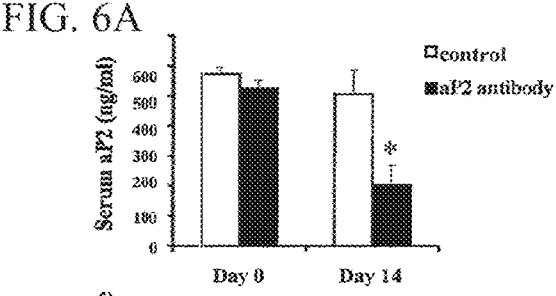
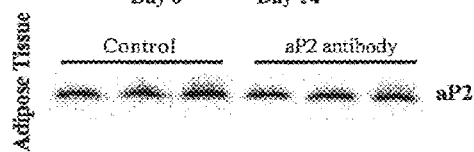
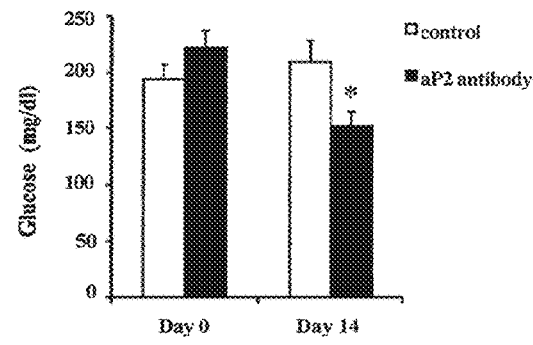
FIG. 6B
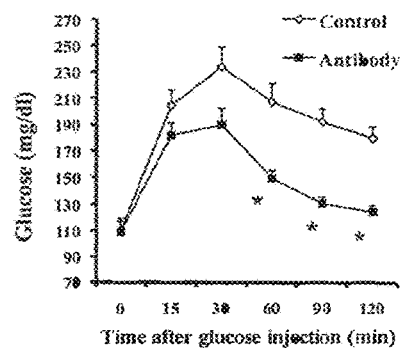
FIG. 6C
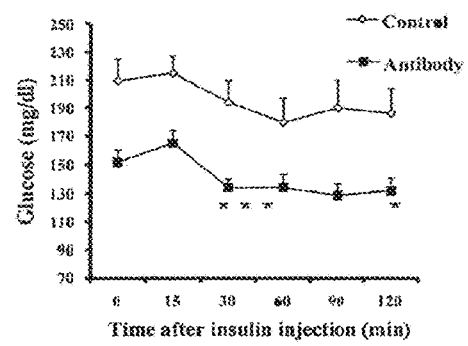
FIG. 6D

FIG. 7E
FIG. 7F
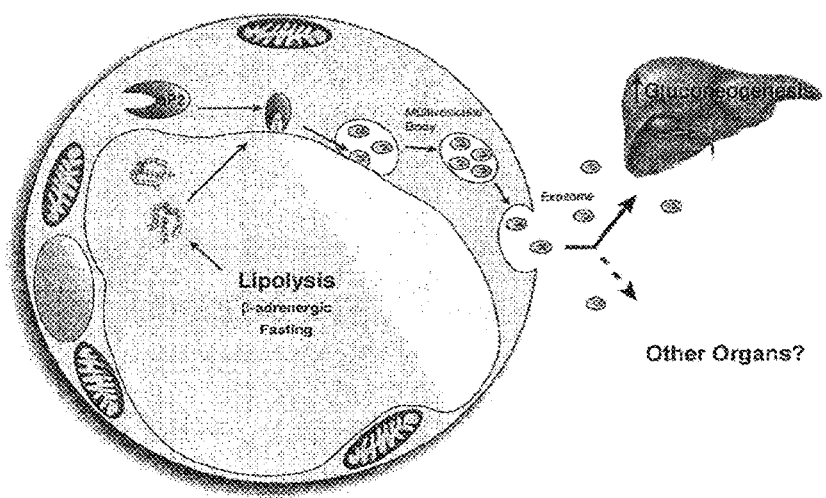
FIG. 7G

Conditioned medium from fat explants

METHODS OF TREATING DIABETES BY AN ADIPOCYTE PROTEIN 2 SPECIFIC ANTIBODY

RELATED APPLICATIONS

This application is a continuation of U.S. application Ser. No. 15/093,508, filed Apr. 7, 2016, which is a continuation of U.S. application Ser. No. 13/203,880, filed Feb. 10, 2012, which is a national stage application, filed under 35 U.S.C. § 371, of International Application No. PCT/US2010/026305, filed Mar. 5, 2010, which claims the benefit of provisional applications U.S. Ser. No. 61/209,251, filed Mar. 5, 2009 and U.S. Ser. No. 61/299,170, filed Jan. 28, 2010, the contents of which are incorporated by reference in their entireties.

STATEMENT OF GOVERNMENT INTERESTS

This invention was made with government support under DK064360 and DK071507 awarded by the National Institutes of Health. The government has certain rights in the invention.

INCORPORATION BY REFERENCE

The contents of the text file named "15020-002US3SequenceListing_ST25.txt" which was created on Dec. 21, 2017, and is 5.36 KB in size, are hereby incorporated by reference in their entirety.

BACKGROUND OF THE INVENTION

Metabolic syndrome or metabolic disease is a term that defines a cluster of metabolic risk factors that come together in a single individual and lead to diabetes and cardiovascular disease. The main features of metabolic syndrome include insulin resistance, hypertension (high blood pressure), cholesterol abnormalities, and an increased risk for clotting. Insulin resistance refers to the diminished ability of cells to respond to the action of insulin in promoting the transport of the sugar glucose, from blood into muscles and other tissues. Patients with this cluster of risk factors are most often overweight or obese.

SUMMARY OF THE INVENTION

The invention is based on the discovery that serum aP2 regulates systemic insulin sensitivity and glucose metabolism. Accordingly, a method of reducing a symptom of metabolic disease is carried out by administering to a subject a composition that binds to and blocks aP2 in the circulation (e.g., blood or serum aP2), by administering a composition that binds to and reduces the amount of aP2 protein in circulation, or by administering an inhibitor of aP2 secretion by a cell. For example, glucose intolerance is reduced following administration of such an inhibitor. Exemplary compositions include antibodies or antigen-specific fragments thereof, small molecules that bind to aP2, as well as compositions that inhibit secretion of aP2 by an adipocyte or macrophage.

A method of preventing or reducing the severity of metabolic disease involves administering to a subject a composition that reduces serum aP2 concentration. In certain embodiments, the method comprises identifying a subject characterized by an elevated level of serum aP2 compared to the aP2 level of a normal, health, age-matched, sex-matched control subject (or pool of subjects). For example, a control subject is lean and is characterized by a serum aP2 level of 20 µg/L, and a subject in need of therapeutic intervention is characterized by a level of aP2 that is elevated. The subject to be treated is overweight, obese, and/or comprises a serum aP2 level greater than 20 µg/L (e.g., 25, 28, 30, 32, 35, 40 or more µg/L aP2 in serum). Subjects are optionally identified as being of normal weight (BMI 18.5-24.9), overweight (BMI 25-29.9), or obese (BMI of 30 or greater).

In each of the therapeutic methods described herein, serum aP2 concentration is reduced by at least 10%, 25% 50%, 75%, 2-fold, 5-fold, 10-fold or more compared to the serum aP2 concentration prior to treatment. In one example, the composition that reduces serum aP2 concentration is an aP2-specific antibody. The antibody is a purified monoclonal or polyclonal antibody. For example, the antibody that binds to antibody-accessible epitopes of aP2, e.g., those highlighted in FIG. 3. Such antibodies bind to epitopes of aP2 that are on surface exposed based on the 3-dimensional structure of the protein in solution (e.g., in blood and serum) as shown in the crystallographic model (FIG. 3). For example, the antibody binds to a discontinuous epitope of aP2. A discontinuous epitope is one in which amino acids are in close proximity in the 3-dimensional structure of the protein (folded), but distant when unfolded. Preferably, the antibody is a monoclonal antibody the binding specificity of which comprises a conformational epitope that is surface accessible on the aP2 molecule as it exists in a bodily fluid such as blood, serum, or plasma. For example, the epitope comprises at least one of the following portions of a human aP2 protein: residues 1-5, residue 22, residues 36-37, residues 46-47, residue 57, residues 59-60, residue 78, residue 80, residue 89, residues 97-101, residues 110-112, residue 122 of SEQ ID NO:3. The antibody optionally binds to two or more of the epitopes (residue or string of residues) as they are exposed on the surface of the aP2 protein in solution. In some examples, the antibody does not bind to denatured aP2 or does not bind to a linear epitope of aP2.

The invention encompasses not only an intact monoclonal antibody and the use thereof, but also an immunologically-active antibody fragment, e. g., a Fab or (Fab)2 fragment; an engineered single chain Fv molecule; or a chimeric molecule, e.g., an antibody which contains the binding specificity of one antibody, e.g., of murine origin, and the remaining portions of another antibody, e.g., of human origin.

Also within the invention is a method of identifying an inhibitor of aP2 secretion. To identify such compounds an aP2-secreting cell such as an adipocyte or macrophage is contacted with a candidate compound and a level of extracellular aP2 detected. A decrease in extracellular aP2 in the presence of the compound compared to the level in the absence of the compound indicates that the compound inhibits aP2 secretion. For example, the level of extracellular aP2 is reduced by at least 10%, 25% 50%, 75%, 2-fold, 5-fold, 10-fold or more.

Screens for inhibitor of aP2 secretion are performed in differentiated adipocytes, which express aP2 abundantly in vitro and in vivo and also have close proximity to adipose tissue in their responses to hormones and other biological stimuli. For example, two approaches are used to perform high-throughput screens. First, a GFP-tagged aP2 is expressed in adipocytes using adenovirus-mediated gene delivery. Inhibitors are applied to cells seeded in 96 well plates and aP2 secretion is determined by measuring fluorescent intensity in conditioned medium. Secondly, a cDNA of aP2 with Flag and HA dual tags is expressed in adipocytes. Secreted aP2 after inhibitor treatments is detected by using an ELISA system. Flag is used to capture aP2 onto plates and HRP-conjugated HA antibody will be used to detected aP2.

The methods and compositions are useful to treat or reduce the severity of clinical disorders that are characterized by aberrantly elevated secreted aP2, e.g., elevated aP2 levels in the blood or serum. Such conditions include metabolic syndrome, glucose intolerance, obesity, diabetes, fatty liver disease, atherosclerosis, and asthma (conditions in which aP2 plays a direct role in the pathology). Increased serum aP2 is also associated with chronic hemodialysis (CD), obstructive sleep apnea (a disorder linked to obesity), lipodystrophy in HIV-infected patients, and lipolysis, which conditions are treated or reduced using the methods and compositions described herein. The methods are also useful to treat or reduce the severity of pathological states such as hypertension, stroke, and neurodegenerative diseases, in which aP2 is indirectly involved.

Inhibitors are used to treat diabetes in humans and other animals, e.g., cats, dogs. For example, the inhibitor is administered to a subject that has been diagnosed as having or at risk of developing Type II diabetes.

Publications, U.S. patents and applications, Genbank/NCBI accession numbers, and all other references cited herein, are herby incorporated by reference.

BRIEF DESCRIPTION OF THE DRAWINGS

FIG. 3 is diagram of discontinuous epitopes based on aP2 crystal structure using using software tool, DiscoTope. Target epitopes are highlighted on the structure, and residues that constitute these epitopes are designated by boxed residues in the amino acid sequence shown below the diagram and are underlined in SEQ ID NO:3 (Table 3, below).

FIG. 6A is a bar graph showing serum aP2 in mice before and after aP2 antibody injection. Top panel, serum aP2 in mice that were maintained on high-fat diet and were injected with pre-immune (Control) or aP2 antibody for two weeks. Serum aP2 levels were determined with an aP2 ELISA. *, $p<0.05$. Bottom panel, total protein extracts of adipose tissue from mice that were maintained on high-fat diet and were injected with pre-immune (Control) or aP2 antibody for two weeks were immunoblotted using anti-aP2 antibody.

FIG. 6B is a bar graph showing glucose levels in obese mice with decreased serum aP2. WT mice maintained on high-fat diet were injected with pre-immune (Control) or aP2 antibody for two weeks and glucose levels were determined after 6 hours of food withdrawal. *, $p<0.05$.

FIG. 6C is a line graph showing glucose tolerance test of mice maintained on high-fat diet that were injected with pre-immune (Control) or aP2 antibody for two weeks.*, $p<0.05$.

FIG. 6D is a line graph showing insulin tolerance test of mice on high-fat diet injected with pre-immune (Control) or aP2 antibody for three weeks. *, $p<0.05$.

FIG. 7E is a photograph of a Western blot exosomes isolated from control adipocytes or adipocytes treated with Forskolin, IBMX, or palmitate were blotted using anti-aP2 or MFG-E8 antibodies.

FIG. 7F is a photograph of a Western blot exosomes isolated from blood of aP2$^{-/-}$, WT mice or WT mice maintained on high-fat diet were blotted using anti-aP2 or MFG-E8 antibodies.

FIG. 7G is a diagram showing the mechanism of aP2 secretion. Upon activation of lipolysis by fasting or (3-adrenergic stimuli, aP2 translocates to surface of lipid droplets where it binds to fatty acids released by lipolysis. Fatty acid binding triggers a signal that targets aP2 to exosomes on which it was released into extracellular space and the blood stream. aP2 then travels to the liver and modulates gluconeogenesis. These figures demonstrate exosome-dependent secretion of aP2.

Figure 1A:
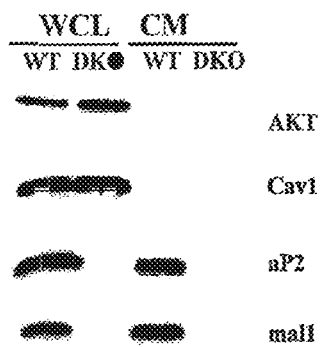
FIG. 1A is a photograph of an electrophoretic gel showing aP2 secretion in adipocytes. Whole cell lysate (WCL) and conditioned medium (CM) from differentiated WT or FABP-deficient (DK) adipocytes were blotted using anti-aP2, mall, caveolin or AKT antibodies.

DETAILED DESCRIPTION aP2 is also known as Adipocyte Fatty Acid Binding Protein (AFABP), Fatty Acid Binding Protein-4 (FABP-4), and Adipocyte Lipid Binding Protein (ALBP). Prior to the invention, aP2 was considered a cytosolic protein. Secreted adipose lipid chaperon, aP2, has now been found to regulate liver glucose metabolism. aP2 was found to be an adipose-secreted protein in cells of mice and other mammals such as humans.

Serum aP2 regulates systemic glucose metabolism. A method of reducing a symptom of a clinical disorder characterized by aberrantly elevated circulating aP2 is carried out by administering to a subject an inhibitor of aP2 secretion by a cell or by administering an aP2 blocking agent. For example, glucose intolerance is reduced following administration of such an inhibitor or agent. Compositions inhibit secretion of aP2 by an adipocyte or macrophage. Alternatively, exemplary compositions such as antibodies bind to circulating aP2, thereby reducing the level or activity of aP2 in blood or serum.

The nucleic acid and amino acid sequences of both mouse and human aP2 are described below.

TABLE 1

Murine aP2 cDNA

```
  1  cctttctcac ctggaagaca gctcctcctc gaaggtttac
     aaaatgtgtg atgcctttgt 61  gggaacctgg aagcttgtct ccagtgaaaa cttcgatgat
     tacatgaaag aagtgggagt 121  gggctttgcc acaaggaaag tggcaggcat ggccaagccc
     aacatgatca tcagcgtaaa 181  tggggatttg gtcaccatcc ggtcagagag tacttttaaa
     aacaccgaga tttccttcaa 241  actgggcgtg gaattcgatg aaatcaccgc agacgacagg
     aaggtgaaga gcatcataac 301  cctagatggc ggggccctgg tgcaggtgca gaagtgggat
     ggaaagtcga ccacaataaa 361  gagaaaacga gatggtgaca agctggtggt ggaatgtgtt
     atgaaaggcg tgacttccac 421  aagagtttat gaaagggcat gagccaaagg aagaggcctg
     gatggaaatt tgcatcaaac 481  actacaaatg tcagtcggat ttattgtttt ttttaaagat
     atgatttttcc actaataagc 541  aagcaattaa ttttttctga agatgcattt tattggatat
     ggttatgttg attaaataaa 601  accttttag actt (SEQ ID NO: 1)
```

TABLE 2

Human aP2 cDNA

```
  1  ggaattccag gagggtgcag cttccttctc accttgaaga
     ataatcctag aaaactcaca 61  aaatgtgtga tgcttttgta ggtacctgga aacttgtctc
     cagtgaaaac tttgatgatt
```

TABLE 2-continued

Human aP2 cDNA

```
121  atatgaaaga agtaggagtg ggctttgcca ccaggaaagt
     ggctggcatg gccaaaccta 181  acatgatcat cagtgtgaat ggggatgtga tcaccattaa
     atctgaaagt accttttaaaa 241  atactgagat ttccttcata ctgggccagg aatttgacga
     agtcactgca gatgacagga 301  aagtcaagag caccataacc ttagatgggg gtgtcctggt
     acatgtgcag aaatgggatg 361  gaaaatcaac caccataaag agaaaacgag aggatgataa
     actggtggtg gaatgcgtca 421  tgaaaggcgt cacttccacg agagtttatg agagagcata
     agccaaggga cgttgacctg 481  gactgaagtt cgcattgaac tctacaacat tctgtgggat
     atattgttca aaaagatatt 541  gttgttttcc ctgatttagc aagcaagtaa ttttctccca
     agctgatttt attcaatatg 601  gttacgttgg ttaaataact ttttttagat ttag
     (SEQ ID NO: 2)
```

TABLE 3

Amino acid sequence of human aP2

MCDAFVGTWKLVSSENFDDYMKEVGVGFATRKVAGMAKPNMIISVNGDVI
TIKSESTFKNTEISFILGQEFDEVTADDRKVKSTITLDGGVLVHVQKWDG
KSTTIKRKREDDKLVVECVMKGVTSTRVYERA (SEQ ID NO: 3)

TABLE 4

Amino acid sequence of mouse aP2

MCDAFVGTWKLVSSENFDDYMKEVGVGFATRKVAGMAKPNMIISVNGDLV
TIRSESTFKNTEISFKLGVEFDEITADDRKVKSIITLDGGALVQVQKWDG
KSTTIKRKRDGDKLVVECVMKGVTSTRVYERA (SEQ ID NO: 4)

Regulation of aP2 Secretion

To confirm that aP2 is released into cell supernatants, conditioned medium and cell lysate from WT or FABP-deficient adipocytes were analyzed in a Western blot for the presence aP2 (FIG. 1A). aP2 was found to be abundantly present in conditional medium while two cytosolic proteins in adipocytes, caveolin and AKT, were undetectable under the same condition (FIG. 1A). Mal 1, a minor isoform of FABPs in adipocytes that shares high homology to aP2, was also released into conditioned medium (FIG. 1A). Collectively, both adipose FABPs are secreted from differentiated adipocytes.

Figure 1B:
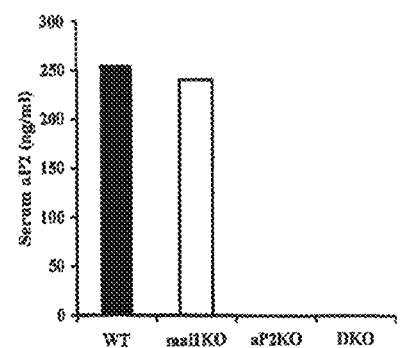
FIG. 1B is bar graph showing serum aP2 concentration of WT, $aP2^{-/-}$ (aP2KO), mal $1^{-/-}$ (mal 1KO) and aP2-mal $1^{-/-}$ (DKO) mice. aP2 levels were determined with an aP2 ELISA as described in experimental procedures.
Figure 1C:
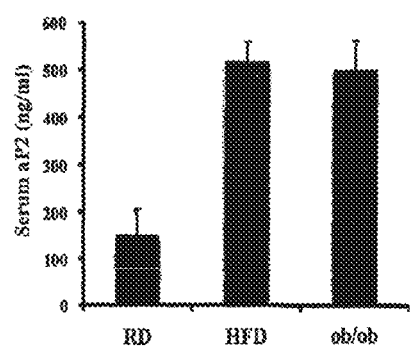
FIG. 1C is a bar graph showing serum aP2 concentration in lean (WT regular diet, RD), dietary obesity (WT high fat diet, HFD) or leptin-deficient genetic obesity in mice (ob).
Figure 1D:
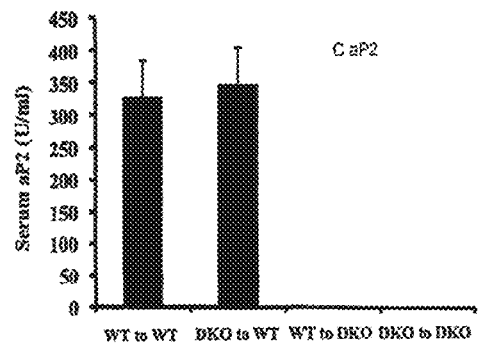
FIG. 1D is a bar graph showing serum aP2 concentration in mice that have undergone bone marrow transplantation. Bone marrow transplantations were performed between WT and FABP-deficient (DKO) mice and serum aP2 were determined with aP2 Elisa. Inset, aP2 blotting of conditioned medium from macrophages transfected with control or aP2 plasmids.

Studies were then carried out to investigate serum aP2 in mice with an aP2 ELISA system. aP2 was present in serum of WT and mal 1$^{-/-}$ mice at a considerable abundance (200 to 300 ng/ml) but was undetectable in serum from aP2$^{-/-}$ or aP2-mal 1$^{-/-}$ mice (FIG. 1B). Serum aP2 was 20 fold more abundant than the adipokine, leptin (10 ng/ml) and was slightly lower than the adipokine, adiponectin (2-5 mg/ml). To explore the long-term serum aP2 regulation in a setting relative to metabolic diseases, serum of lean and obese mice that are induced by either high-fat diet feeding or leptin deficiency was compared. Serum aP2 was profoundly increased in both obesity models (FIG. 1C), indicating that secreted aP2 may be functional and related to altered metabolic regulation under these pathological conditions. aP2 is expressed in both adipocytes and macrophages and loss-of-function mutation of aP2 in either site protects mice from developing metabolic disease (Furuhashi et al., 2008, J Clin Invest. 118:2640-50; Maeda et al., 2005, Cell Metab 1, 107-119.)

aP2 was also found to be secreted by macrophages (FIG. 1D inset). Obese mice accumulate macrophages in adipose tissue which contribute to insulin resistance. Therefore, increased serum aP2 is the result of increased aP2 release from either cell type. To determine which locus is responsible for the increased serum aP2 upon obesity, bone marrow was transplanted between WT and FABP-deficient mice. Serum aP2 in these mice was examined. Bone marrow-derived cells from WT mice cannot sustain a detectable level of serum aP2 in FABP-deficient mice (FIG. 1D), indicating that adipocytes, instead of hematopoietic cells, are the prime contributor of serum aP2 in mice.

Serum aP2 Regulates Systemic Glucose Metabolism

Figure 2A:
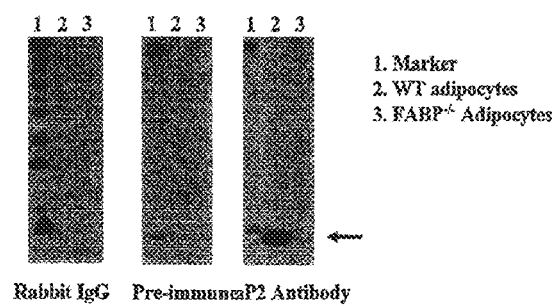
FIG. 2A is a photograph of an electrophoretic gel showing the results of a Western blot assay using an aP2-specific antibody. Cell lysate from WT or FABP-deficient adipocytes were blotted using control rabbit IgG, pre-immune serum or aP2 antibodies.
Figure 2B:
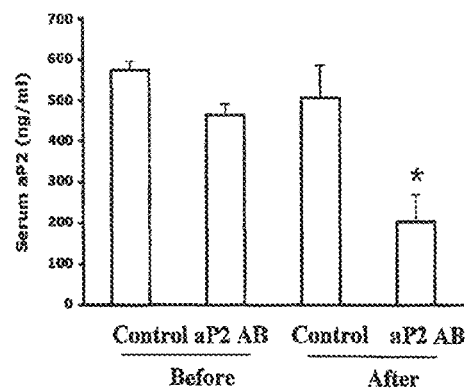
FIG. 2B is a bar graph showing serum aP2 concentration in mice before and after aP2 antibody administration. Serum aP2 in mice that were maintained on high-fat diet and were injected with control or aP2 antibodies for two weeks were analyzed with an aP2 ELISA.
Figure 2C:
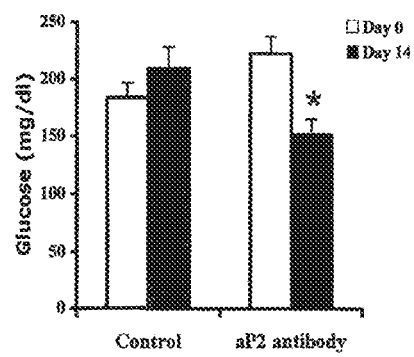
FIG. 2C is a bar graph showing glucose levels in mice with decreased serum aP2. WT mice maintained on high-fat diet were injected with control IgG or aP2 antibodies for two weeks and body weights determined before and after injections.
Figure 2D:
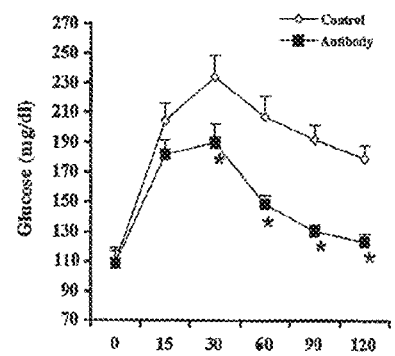
FIG. 2D is a line graph showing the results of a glucose tolerance test of mice injected with control or aP2 antibodies for two weeks.
Figure 2E:
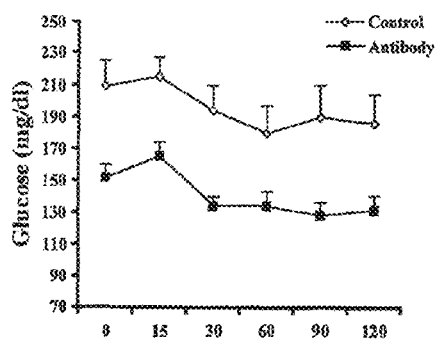
FIG. 2E is a line graph showing the results of an insulin tolerance test of mice injected with control or recombinant aP2 for two weeks.
Figure 2F:
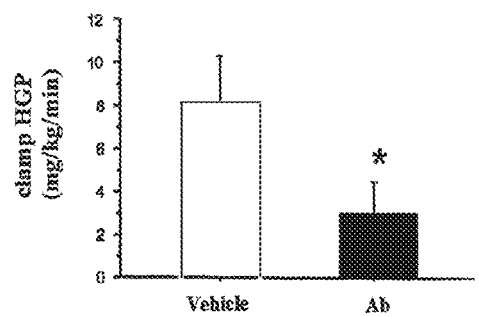
FIG. 2F is a bar graph showing clamp hepatic glucose production rate (cHGP) in mice injected with control or aP2 antibody during hyperinsulinemic-euglycemic clamp study.

Adipoycte-secreted hormones (i.e., adipokines) play a role in glucose and lipid metabolism (Rosen et al., 2006, Nature 444: 847-853). Since serum aP2 is increased under obesity and diabetes conditions, experiments were carried out to determine whether decreasing serum aP2 in obesity would improve glycemic control if increased aP2 plays a role in altered glucose metabolism as seen in obesity. To efficiently deplete serum aP2, an antibody specifically recognizing aP2 was developed. Studies using the antibody confirmed that it specifically detected aP2 at very high sensitivity (FIG. 2A). This antibody was injected into obese mice. The mice were induced to obesity by high-fat feeding for 16 weeks. The administration of aP2 antibody efficiently and rapidly suppressed serum aP2 concentration (FIG. 2B). The aP2 antibody treatment did not alter body weight of these mice but caused a significant decrease in blood glucose level upon two weeks of administration (FIG. 2C). Mice injected with aP2 antibody also have dramatically improved glucose disposal rate and improved insulin response determined by glucose and insulin tolerance tests (FIGS. 2D and 2E). In fact, aP2 antibody treatment essentially abolished glucose intolerance associated with dietary obesity in these mice, indicating that reducing serum aP2 confers a clinical benefit for those suffering from type II diabetes.

To determine the loci of aP2 action in vivo, hyperinsulinemic-euglycemic clamp studies were performed. Mice receiving aP2 antibody injections were found to have decreased hepatic glucose production (FIG. 2G) indicating that liver is a major target of the glucose-lowering effects of aP2 antibodies.

Figure 2G:
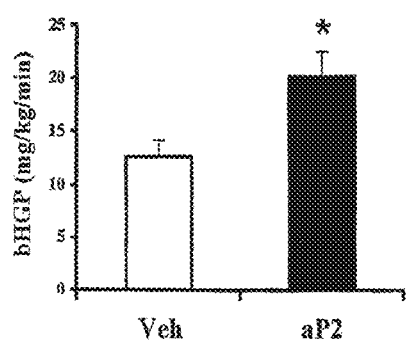
FIG. 2G is a bar graph showing basal hepatic glucose production rate (bHGP) in mice injected with control or aP2 antibody during hyperinsulinemic-euglycemic clamp study.

In reciprocal experiments to determine the metabolic output of increased serum aP2, purified recombinant aP2 was produced and infused into conscious FABP-deficient mice. A hyperinsulinemic-euglycemic clamp study was then performed to monitor whole-body glucose metabolism of these mice. FABP$^{-/-}$ mice infused with aP2 had significantly increased basal hepatic glucose production (bHGP) (FIG. 2G). This is a profound effect considering that these mice have been only infused with aP2 for 4 hrs at the time when bHGP was determined.

Figure 2H:
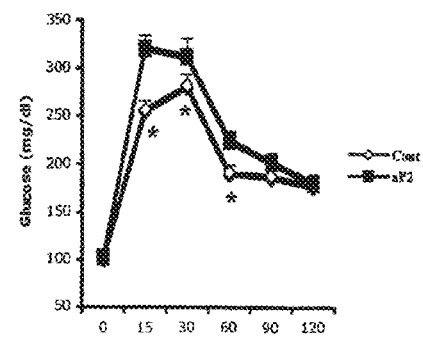
FIG. 2H is a line graph showing basal hepatic glucose production rate (bHGP) in FABP-deficient mice that were infused with control proteins or recombinant aP2 during hyperinsulinemic-euglycemic clamp study.

To further investigate the effects of increased serum aP2, recombinant aP2 was injected intraperitoneally into WT mice maintained on regular chow diet. aP2 administration did not alter body weight of the mice but the otherwise lean and healthy mice, developed glucose intolerance as determined by glucose tolerance tests after receiving aP2 injection for two weeks (FIG. 2H). This observation indicated that serum aP2 regulates systemic glucose metabolism and increased serum aP2 alone in a short period time can cause impaired glucose disposal independent of body weight changes and dietary contribution.

Adipose Tissue and Metabolic Disorders

Accumulating evidence in the last fifteen years has established adipose tissue as one of the largest endocrine organs responsible for metabolic regulation. The effects of fat tissue on systemic energy homeostasis are mediated by a variety of hormones. Adipose tissue in obese subjects has also been shown to produce a growing list of inflammatory cytokines, and chronic adipose inflammation has emerged as an important feature linking obesity and related metabolic disorders. Thus, in both physiological and pathological contexts, adipose tissue represents a key locus where nutrient and endogenous signaling molecules interact and integrate, ultimately resulting in systemic regulation of energy homeostasis. As the major lipid storage site of the body, adipose tissue is also the key supplier of energy during fasting. Adipose lipolysis contributes the majority of fatty acids to the serum, which are taken up and oxidized in muscle and also activate glucose production in liver. The lipolysis-associated elevation of hepatic glucose production is a critical homeostatic phenomenon known to be dysregulated in obesity. Prior to the invention, the mechanism by which this process is signaled between adipose tissue and the liver was not completely understood.

Earlier studies have demonstrated that adipose tissue lipid chaperones, and in particularly aP2, are critical integrators of lipid signals with metabolic and inflammatory responses. Mice deficient in these chaperones, known as fatty acid binding proteins (FABP), exhibit marked protection against a multitude of metabolic abnormalities associated with obesity, including insulin resistance, type 2 diabetes, hepatosteatosis, and atherosclerosis. The effects of FABP-deficiency in adipose tissue are systemic, as evidenced by the global changes in metabolic pathways and responses of liver, muscle and other tissues.

In the search for fat-secreted molecules that might mediate the beneficial effects of FABP-deficient adipose tissue, a fatty acid, C16:1n7-palmitoleate, was discovered. This fatty acid potently increases muscle insulin action, while simultaneously suppressing fatty infiltration of the liver. On the other hand, the role of peptide hormones in FABP deficiency is less clear. FABP-null mice have altered levels of leptin and adiponectin, but detailed investigation confirmed that neither was responsible for the improved glucose and lipid metabolism of FABP-deficient mice.

aP2 itself has been identified in human serum, raising the possibility that serum aP2 might be involved in metabolic regulation in obesity. The improved glucose metabolism in FABPdeficient mice could occur at least in part as a result of the loss of serum aP2, if this molecule is indeed secreted from adipocytes in a regulated manner.

The following materials and methods were used to generate the data described herein.

Animals

Mice with homozygous null mutations in aP2 and mal1 were backcrossed more than 12 generations into a C57BL/6J genetic background. Mice were maintained on regular chow diet (RD) or placed on high-fat diet (Research Diets, Inc) at 4 weeks of age for 20 weeks to induce dietary obesity. Leptin-deficient (ob/ob) mice were purchased from the Jackson laboratory. All mice were maintained on a 12-hour light and dark cycle. Glucose and insulin tolerance tests using standard methods.

Quantification of Serum aP2

Blood was collected from mice by tail bleeding after 6 hours of food withdrawal and spun in a microcentrifuge at 13,000 rpm for 30 minutes. Serum aP2 was determined with an ELISA system (Biovendor Inc.). To monitor nutritional regulation of serum aP2, blood samples were collected from mice immediately prior to the start of dark cycle after which animals were placed in cages without food. After 24 hours of fasting, a second set of blood samples were collected and food was provided. Final blood sampling was performed 4 hours after re-feeding. To determine aP2 levels during lipolysis, blood was collected from 12 mice at baseline levels. After this, 6 mice were injected with isoproterenol (10 mg/kg body weight) and the other 6 received vehicle control. Blood samples were collected 15 min following injection for aP2 measurement.

Bone Barrow Transplantation

Six-week-old recipient mice were irradiated with two 5 Gy doses (total 10 Gy) from a cesium source separated by a 4-hour interval in order to minimize radiation toxicity. Bone marrow was collected by flushing the femurs and tibias from sex-matched donor mice (6-8 weeks of age) with Gibco RPMI 1640 medium (Invitrogen, Carlsbad, Calif.). Four hours after the second irradiation, $5 \times 10^6$ bone marrow cells in 0.2 ml medium were injected in the retro-orbital venous plexus. Starting one week before and 4 weeks following bone marrow transplantation, 100 mg/l neomycin and 10 mg/l polymyxin B sulfate were added to the acidified water.

Production, Purification, and Administration of Recombinant aP2 and aP2 Antibody Recombinant aP2 or control Gus protein with 6×His tag was produced in *E. coli* and purified with B-PER 6×His Spin Purification Kit (Pierce Biotechnology, Inc). Proteins were further purified by removing endotoxin with a commercial system (Lonza Inc.). 100 μg of control or aP2 protein was injected into WT mice maintained on regular chow diet twice a day for two weeks. The rabbit polyclonal antibody against mouse aP2 was produced using recombinant, full-length aP2 protein and the antibody was purified from serum of the final bleed using the NAb™ Spin system (Pierce Biotechnology, Inc). Pre-immune serum was purified similarly and used as control. Purified antibody was diluted in saline to 1 μg/μl and injected into mice maintained on high-fat diet (Research diet, Inc) at a dose of 50 mg/kg.

Vector Construction and Transfection

Flag-tagged GFP (plasmid ID 10825) and AKT (plasmid ID 9021) were obtained from Addgene. Flag-tagged full-length and portal-less aP2 were cloned in pEGFP-C1. aP2 K22, 59I variant was created with the Quickchange mutagenesis system (Stratagene). HEK 293 cells were transfected with the indicated constructs using Lipofectamine 2000 (Invitrogen Corporation).

Cell Culture

HEK 293 cells were maintained in DMEM with 10% fetal bovine serum. FABP-deficient cell lines were established as previously described. Cao, H. et al. Identification of a lipokine, a lipid hormone linking adipose tissue to systemic metabolism. *Cell* 134, 933-944 (2008). Makowski, L. et al. Lack of macrophage fatty-acid-binding protein aP2 protects mice deficient in apolipoprotein E against atherosclerosis. *Nat Med* 7, 699-705 (2001). Pre-adipocytes were maintained in DMEM with 10% bovine calf serum and differentiated into adipocytes in DMEM with 10% cosmic calf serum (CCS) using a standard differentiation protocol. To induce lipolysis, differentiated adipocytes were treated with forskolin at 20 nM, or IBMX 1 mM/dibutyryl cAMP 1 mM for one hour. For lipid treatments, 0.25 mM palmitate or stearate was dissolved in DMEM with 10% CCS and added to adipocytes cultured in 12-well plates. At the end of one hour, the medium was replaced with the same lipid-containing medium, and conditioned medium was collected an additional hour later. To collect fat explants, epididymal adipose tissue depots were dissected from mice and rinsed twice in PBS. Adipose tissue samples were then transferred into DMEM with 10% CCS and minced into an average size of 1 to 2 mm. The tissue explants were washed extensively with DMEM and cultured in DMEM containing 10% CCS. Lipolysis was induced in the same manner as adipocytes.

Fluorescent Microscopy

Cells were cultured on cover-slips in 6-well tissue culture plates and fixed in 4% paraformaldehyde. Nuclei were stained with DAPI and cover-slips were mounted on slides with the ProLong Gold antifade reagents (Invitrogen Corporation). Imaging was performed on a Zeiss Observor Z1 fluorescent microscope.

Exosome Isolation

To isolate exosomes from adipocytes, conditioned medium was collected and centrifuged at 1,200 g for 10 minutes. The medium was then filtered through a 0.45 μm filter, centrifuged twice at 10,000 g for 30 minutes, and loaded onto 20% sucrose gradients. The exosome fraction was pelleted by centrifugation at 100,000 g for 150 minutes. To isolate exosomes from serum, blood was collected from mice and centrifuged in a microcentrifuge at top speed for 30 minutes to collect plasma. Plasma was diluted in equal volume of PBS and loaded on to a 20% sucrose gradient and exosomes were pelleted by centrifugation at 200,000 g for 90 minutes.

RNA Extraction and Quantitative Real-Time PCR Analysis

Total RNA was isolated from liver tissues using Trizol reagent (Invitrogen). Reverse transcription was carried out with a superscript first-strand cDNA synthesis system (Applied Biosystems Inc.) using 1 μg of RNA. Quantitative, real-time RT-PCR was performed on a PCR thermal cycler (Applied Biosystems Inc.). The PCR program was: 2 min 30 s at 95° C. for enzyme activation, 40 cycles of 15 s at 95° C., 30 s at 58° C., and 1 min at 72° C. for extension. Melting curve analysis was performed to confirm the real-time PCR products. All quantitations were normalized to the 1 8S rRNA. Primer sequences used were the following: PEPCK, forward: CTGCATAACGGTCTGGACTTC(SEQ ID NO: 5), reverse: CAGCAACTGCCCGTACTCC (SEQ ID NO: 6); G6P, forward: CGACTCGCTATCTCCAAGTGA (SEQ ID NO:7), reverse: GTTGAACCAGTCTCCGACCA (SEQ ID NO: 8).

Coomassie Staining, Immunoprecipitation and Immunoblotting

Tissue protein lysate and conditioned medium from adipocytes were separated on SDS-PAGE gels and stained with Coomassie (Biorad Laboratory), or were detected with immunoblotting using the following antibodies: adiponectin from Santa Cruz Biotechnology, MFG-E8 from Calbiochem, caveolin-1 from BD Bioscience, AKT from Cell Signaling Technology. Flag-tagged aP2 was immunoprecipated using 4 ml of conditioned medium from transfected HEK 293 cells after incubation with 30 μl Flag agarose beads (Sigma) overnight at 4° C. Proteins bound to agarose beads were eluted with SDS loading buffer and resolved with SDS-PAGE.

Intralipid and aP2 Infusion

Four days prior to experiments, mice were anesthetized with an intraperitoneal injection of ketamine (90 mg/kg body weight) and xylazine (10 mg/kg body weight). Their right jugular vein was catheterized with PE-10 polyethylene tubes (inside and outside diameters, 0.28 mm and 0.61 mm, respectively; Becton Dickinson, Franklin Lakes, N.J.) filled with heparin solution (100 USP U/ml). The distal end of the catheter was tunneled under the skin, exteriorized in the interscapular area, and then knotted for immobilization.

The mice were fasted overnight before the experiments and were infused with Intralipid at 3 ml/kg/h (Abbott) and heparin (6 U/h) for 5 hours. Recombinant aP2 was infused at 8 µg/kg/min for 5 hours.

Hyperinsulinemic-Euglycemic Clamp Studies

Mice were catheterized as described above. Hyperinsulinemic-euglycemic clamps were performed by a modification of a reported procedure[15]. After an overnight fast, HPLC purified [3H]-glucose (0.05 µCi/min; PerkinElmer Life and Analytical Sciences, Boston, Mass.) was infused during the 2-h basal period, and blood samples were collected at the end to estimate the rate of basal hepatic glucose production. After the basal period, a 120-min hyperinsulinemic-euglycemic clamp was conducted with a primed-continuous infusion of human insulin (Humulin R; Eli Lilly, Indianapolis, Ind.) at a rate of 12.5 mU/kg/min. Blood samples were collected at 20-min intervals for the immediate measurement of plasma glucose concentrations, and 25% glucose was infused at variable rates to maintain plasma glucose at basal concentrations. Insulin-stimulated whole-body glucose turnover was estimated with a continuous infusion of [3-$^3$H]-glucose throughout the clamps (0.1 µCi/min). All infusions were performed using flow-controlled microdialysis pumps (CMA/Microdialysis, North Chelmsford, Mass.). Blood samples were taken at 80, 85, 90, 100, 110, and 120 min after the start of clamps for the determination of plasma [$^3$H]-glucose, and $^3$H2O concentrations. At the end of clamps, animals were sacrificed. Within 5 min, liver tissue was harvested and stored at −80° C. for further analysis.

aP2 is Secreted from Adipocytes In Vitro

Figure 4A:
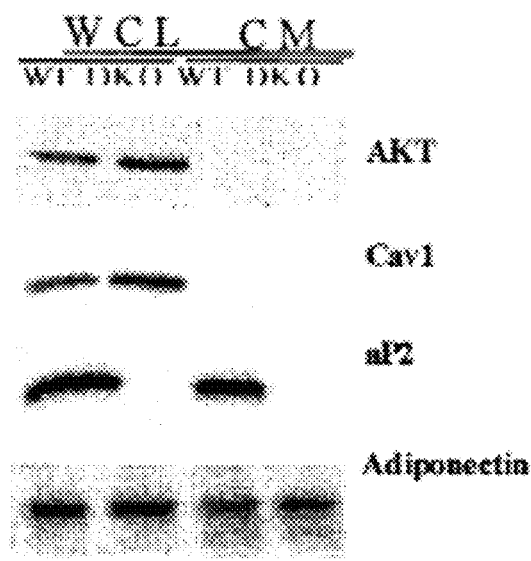
FIG. 4A is a photograph of an electrophoretic gel showing aP2 secretion in adipocytes. Whole cell lysate (WCL) and conditioned medium (CM) from differentiated WT or aP2-mal $1^{-/-}$ (DKO) adipocytes were blotted using anti-aP2, caveolin, AKT or adiponectin antibodies.
Figure 4B:
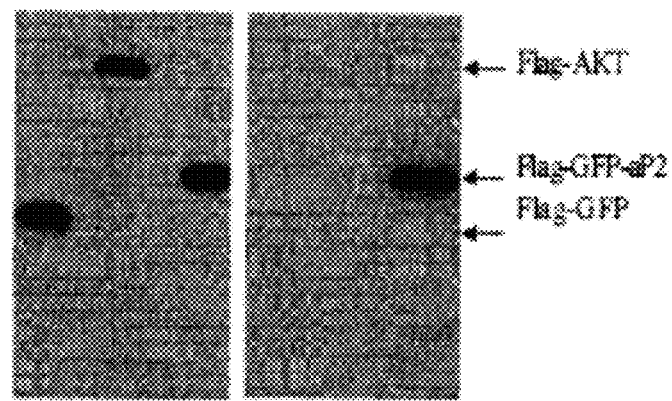
FIG. 4B is a photograph of an electrophonetic gel showing aP2 secretion in HEK 293 cells. Whole cell lysate (WCL) or immunoprecipated conditioned medium (CM) from HEK 293 cells transfected with Flag-AKT, Flag-GFP-aP2 or Flag-GFP plasmids were blotted using anti-Flag antibody.
Figure 4C:
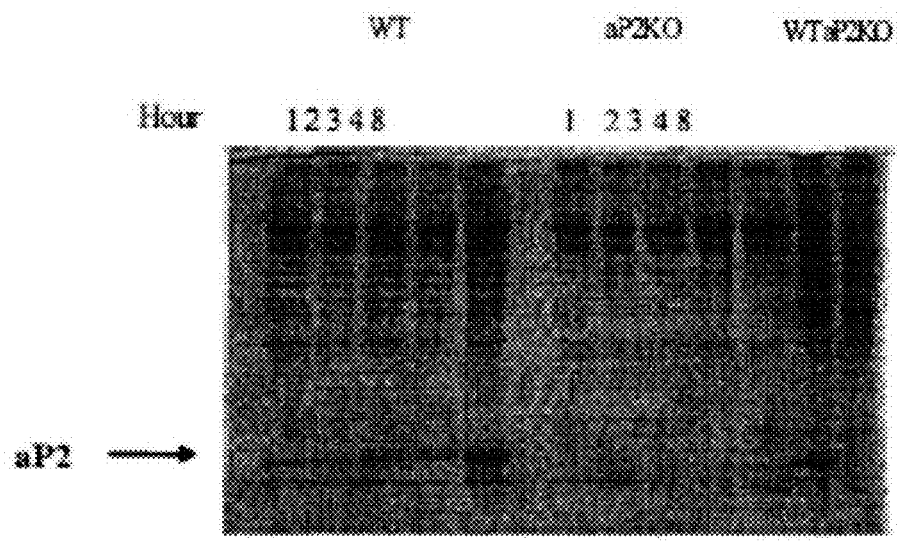
FIG. 4C is a photograph of an electrophonetic gel showing Conditioned medium were collected from WT or $aP2^{-/-}$ adipocytes at indicated time points since medium change. The medium were resolved with SDS-PAGE and stained with Coomassie blue to examine all abundant proteins present in the medium. Serum aP2 of WT, $aP2^{-/-}$ (aP2KO), mal $1^{-/-}$ (mal 1KO) and aP2-mal $1^{-/-}$ (DKO) mice.

Since its initial identification, aP2 has been considered a cytosolic protein but was recently identified by a proteomics screen in the supernatant of differentiated 3T3-L1 adipocyte and subsequently in human serum. Studies were carried out to determine whether aP2 is specifically secreted by adipocytes or released during cell turnover. Examination of aP2 levels in the conditioned medium and cell lysate collected from wild type (WT) or FABPdeficient adipocytes revealed the abundant presence of this protein in the conditioned medium of WT cells (FIG. 4A). In contrast, two abundant cytosolic proteins in adipocytes, caveolin and Akt, were undetectable under the same conditions, suggesting the possibility of active secretion (FIG. 4A). However, as one of the most abundant cytosolic proteins in adipocytes, the presence of aP2 in conditioned medium could still be due to non-specific release resulting from cell death and/or lysis. To determine the nature of aP2's exit from cells, Flag-tagged aP2 was transfected into HEK 293 cells along with similarly tagged GFP and Akt as controls and carefully titrated the amounts of each plasmid to ensure that all proteins were expressed at similar levels inside cells (FIG. 4B). Both conditioned medium and cell lysate were probed with anti-Flag antibody to eliminate any variation that might be introduced by differing sensitivities among antibodies. In these experiments, aP2 was readily detectable in the conditioned medium while GFP and AKT were undetectable under the same conditions (FIG. 4B). These data indicated that aP2 is actively secreted and that its presence in conditioned medium was not due to non-specific cell lysis or death. To investigate the relative abundance of aP2 among all adipocytesecreted proteins, conditioned medium from adipocytes was resolved by one-dimensional electrophoresis. These data revealed that aP2 is one of the most abundant proteins secreted from adipocytes (FIG. 4C) present at a level comparable to that of adiponectin and indicated that aP2 has an important biological function outside of cells.

Regulation of aP2 Secretion In Vivo

Figure 4D:
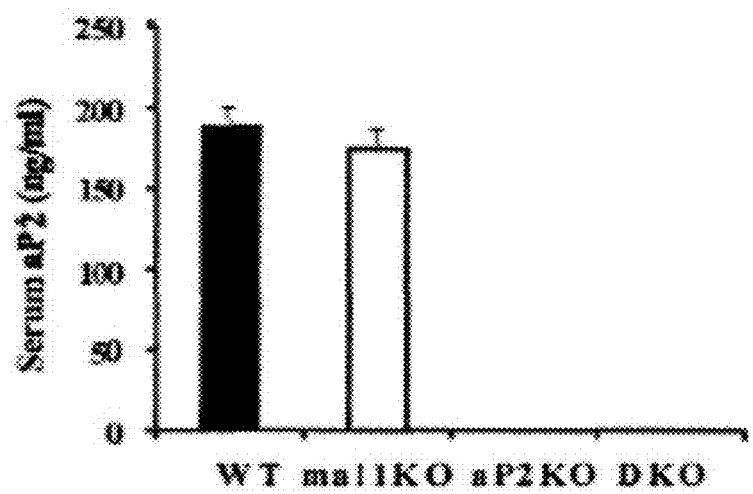
FIG. 4D is a bar graph showing aP2 levels determined with an aP2 ELISA.
Figure 4E:
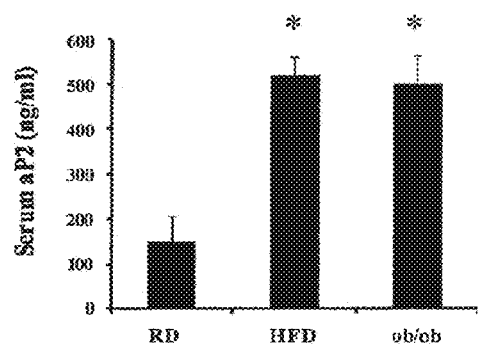
FIG. 4E is a bar graph showing Serum aP2 in mice of lean (WT regular diet, RD), dietary obesity (WT high fat diet, HFD) or leptin-deficient genetic obesity (ob/ob). *, $p<0.05$.

To examine the regulation of aP2 secretion, the serum levels of aP2 in mice were examined by utilizing an ELISA system. In WT and mal 1$^{-/-}$ mice, aP2 was present at a considerable levels (100 to 300 ng/ml) in serum, but was undetectable in aP2$^{-/-}$ and aP2 mal 1$^{-/-}$ controls (FIG. 4D). Serum aP2 is 10 to 30-fold more abundant than leptin (around 12.5 ng/ml), but still significantly lower than adiponectin levels (5-10 µg/ml). To explore the regulation of serum aP2 in the context of metabolic disease, the serum profiles of lean mice and both genetic and diet induced mouse models of obesity were compared. Serum aP2 was markedly (µ4 fold) increased in both obesity models (FIG. 4E), suggesting that aP2 might be related to altered metabolic regulation under these pathological conditions. Consistently, increased circulating aP2 levels have been reported to be associated with obesity in humans.

Figure 4F:
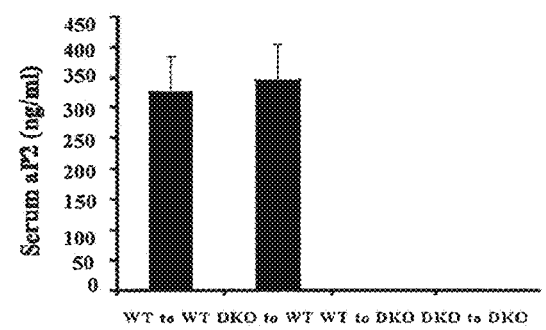
FIG. 4F is a bar graph showing Serum aP2 in mice that have undergone bone marrow transplantation. Bone marrow transplantation was performed between WT and aP2-mal $1^{-/-}$ (DKO) mice and serum aP2 levels were determined with an aP2 ELISA.
Figure 8:
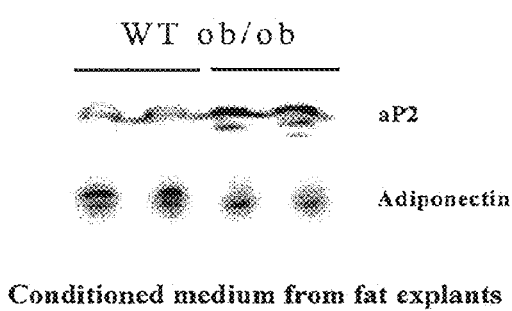
FIG. 8 is an immunoblot showing aP2 secretion from fat explants of WT and ob/ob mice. aP2 secretion in fat explants of lean and obese mice. Fat explants were collected from WT mice maintained on regular diet or ob/ob mice and were thoroughly washed. Fresh medium was added and incubated overnight and collected for immunoblotting analysis using anti-aP2 or adiponectin antibodies.

Increased aP2 levels during obesity could be due to elevated aP2 expression, expanded fat mass or increased aP2 secretion. While it is known that obesity does not have a strong impact on overall aP2 expression, studies were carried out to distinguish whether an increased volume of fat mass or a dysregulation of secretion was responsible for the elevated levels of serum aP2 observed in obese mice. Fat explants were collected from lean and obese mice (ob/ob) and aP2 release ex vivo in an explant culture was examined. aP2 secretion from an equal mass of fat explanted from obese mice was significantly higher than that from lean controls, indicating that obese mice have dysregulated aP2 secretion (FIG. 8). Adiponectin secretion was significantly reduced in obese explants, verifying the fidelity of this system in capturing the secretory profile of adipose tissue (FIG. 8).

aP2 is expressed in both adipocytes and macrophages and a loss-of-function mutation of aP2 in either cell type can contribute to the improved metabolic responses in mice. Since obese mice accumulate macrophages in adipose tissue, an event that has been proposed to contribute to insulin resistance, increased aP2 in serum and in fat explants could be due to increased aP2 release from adipose tissue macrophages. To determine the cell type responsible for the increased serum aP2 in the context of obesity, bone marrow transplantation between WT and FABP-deficient mice was performed. An examination of serum revealed bone marrow-derived cells from WT mice could not sustain a detectable level of serum aP2 in FABP-deficient mice (FIG. 4F). This finding supported the idea that adipocytes but not hematopoietic cells, are the predominant contributor of serum aP2 in mice, and that aP2 is a novel adipokine with an altered serum profile in obesity.

aP2 Secretion is Regulated by Lipolysis-Released Fatty Acids

Figure 5A:
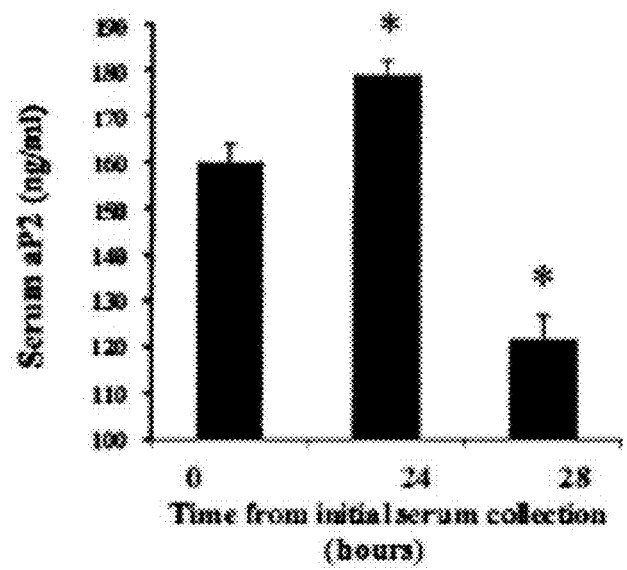
FIG. 5A is a bar graph showing Serum aP2 in mice of ad libitum feeding (0), 24 hours fasting (24) or 4 hour re-feeding after 24 hours fasting (28). *, $p<0.05$.

Studies were carried out to evaluate whether a metabolically active protein secreted from adipocytes would be regulated by metabolic status and nutrient fluctuations. Such regulation could shed light on the mechanism of dysregulation under pathological conditions. Thus, experiments were carried out to determine whether serum aP2 levels change in response to fasting and re-feeding. The circulating aP2 levels in mice fasted for 24 hours were significantly increased compared to levels during ad libitum feeding, but were quickly suppressed after 4 hours of re-feeding (FIG. 5A). Therefore, nutrient and metabolic status can modulate serum aP2 levels, which in turn suggests that aP2 might be part of a systemic program that regulates energy homeostasis.

Figure 5B:
FIG. 5B is a photograph of an electrophonetic gel showing aP2 in conditioned medium (CM) or whole cell lysate (WCL) of adipocytes treated with IMBX/dbcAMP (I/C) and insulin (Ins).
Figure 5C:
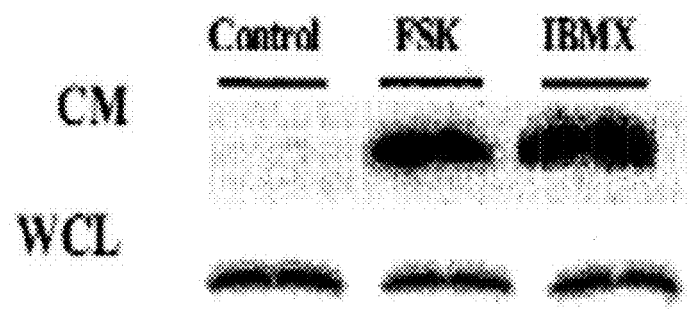
FIG. 5C is a photograph of an electrophonetic gel showing aP2 in conditioned medium or whole cell lysate of fat explants treated with forskolin (FSK) or IBMX.
Figure 5D:
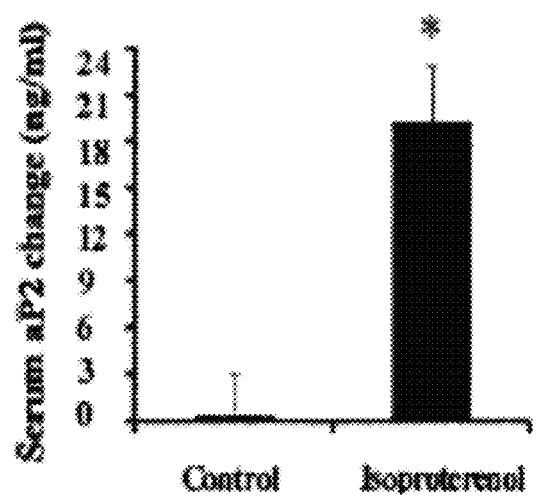
FIG. 5D is a bar graph showing Serum aP2 levels in mice injected with saline (Control) or Isoproterenol to induce lipolysis as compared to their initial aP2 levels.

The primary function of adipose tissue in energy homeostasis is providing fatty acids via lipolysis for other tissues during fasting. To investigate whether aP2 secretion is linked to lipolysis, pre-adipocytes were differentiated and lipolysis stimulated in the cells. Isobutylmethylxanthine (IBMX) and dbcAMP treatment induced a robust increase in aP2 secretion from adipocytes within an hour (FIG. 5B). When cells were co-treated with insulin to suppress lipolysis, aP2 secretion was suppressed (FIG. 5B). To further investigate aP2 secretion from adipocytes in a tissue environment, fat explants were harvested and cultured ex vivo. aP2 secretion was examined under baseline conditions or upon stimulation of lipolysis. IBMX or forskolin treatment caused a very substantial increase in aP2 secretion (FIG. 5C) confirming that this process is tightly linked to lipolysis. To explore the impact of lipolysis on aP2 secretion in vivo, mice were injected with isoproterenol, a (3-adrenergic receptor agonist that strongly activates lipolysis. Mice receiving isoproterenol showed a rapid increase in serum aP2 levels compared to control animals treated with vehicle (FIG. 5D) indicating that aP2 secretion is regulated by lipolysis in vivo and that the elevated serum aP2 in mice during fasting is caused by increased lipolytic activity in adipose tissue.

Figure 5E:
FIG. 5E is a photograph of an electrophonetic gel showing aP2 in conditioned medium or whole cell lysate of adipocytes treated with palmitate (C 16) or stearate (C 18).
Figure 5F:
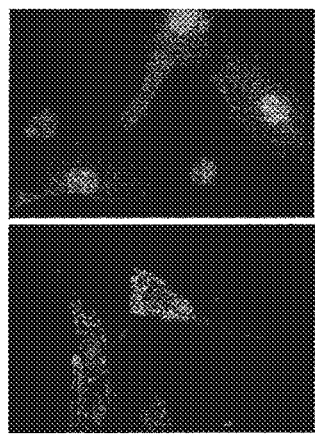
FIG. 5F is a photomicrograph showing preadipocytes expressing GFP-aP2 were cultured in regular medium (control) or medium containing 0.5 mM palmitate overnight.

To further investigate whether fatty acids released by lipolysis regulate aP2 secretion, adipocytes were treated with palmitate and stearate. Both lipids significantly increased aP2 secretion (FIG. 5E). Fatty acid treatment also caused translocation of a GFP-tagged aP2 to lipid droplets (FIG. 5F) suggesting that lipids also regulate aP2's cellular localization and may target it to a secretory pathway.

Figure 5G:
FIG. 5G is a photograph of an electrophonetic gel showing aP2 in conditioned medium and whole cell lysate of adipocytes treated with IBMX/dbcAMP (I/C) or DEUP.

Lipolysis is a complicated process involving multiple signaling pathways, many of which could potentially regulate aP2 secretion. To determine the significance of fatty acids in lipolysis-induced aP2 secretion, adipocytes were treated with diethylumbelliferyl phosphate (DEUP), a triglyceride hydrolase inhibitor, following induction of lipolysis to prevent fatty acid release from triglyceride (TG) stores. DEUP treatment completely blocked lipolysis-induced aP2 secretion, indicating that fatty acid release is required for aP2 secretion (FIG. 5G).

Figure 5H:
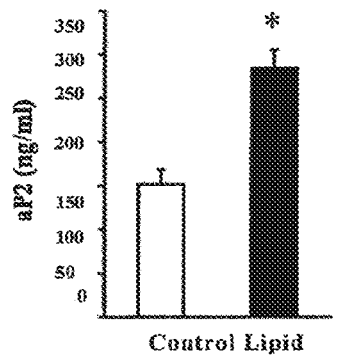
FIG. 5H is a bar graph showing serum aP2 in mice infused with saline (Control) or Intralipid/heparin (Lipid) for 5 hours. These figures demonstrate aP2 secretion is activated by lipolysis-released fatty acids.

To test the effect of fatty acids on aP2 secretion in vivo, an intralipid/heparin infusion was performed in live conscious mice. Increased serum fatty acids by Intralipid infusion also induced aP2 secretion (FIG. 5H) indicating that fatty acids stimulate aP2 secretion in vivo.

Serum aP2 Critically Regulates Hepatic Glucose Metabolism In Mice

Mice deficient in FABPs are protected from multiple components of metabolic syndrome, particularly type 2 diabetes. Elevated serum aP2 in humans has also been reported to be associated with diabetes, cardiovascular disease and other metabolic disorders. However, prior to the invention, a causal relationship between circulating aP2 and lipid and/or carbohydrate metabolism had not been established. The tight coupling of aP2 secretion to lipolysis suggests that serum aP2 might have synergistic effects on metabolic regulation resulting from fluctuations in fatty acids.

Figure 6E:
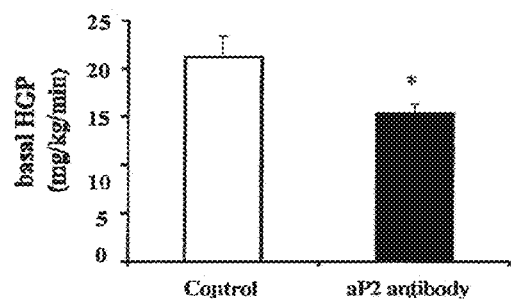
FIG. 6E is a bar graph showing basal hepatic glucose production rate (bHGP) in mice on high-fat diet injected with pre-immune (Control) or aP2 antibody during hyperinsulinemic-euglycemic clamp study. *, $p<0.05$.
Figure 9:
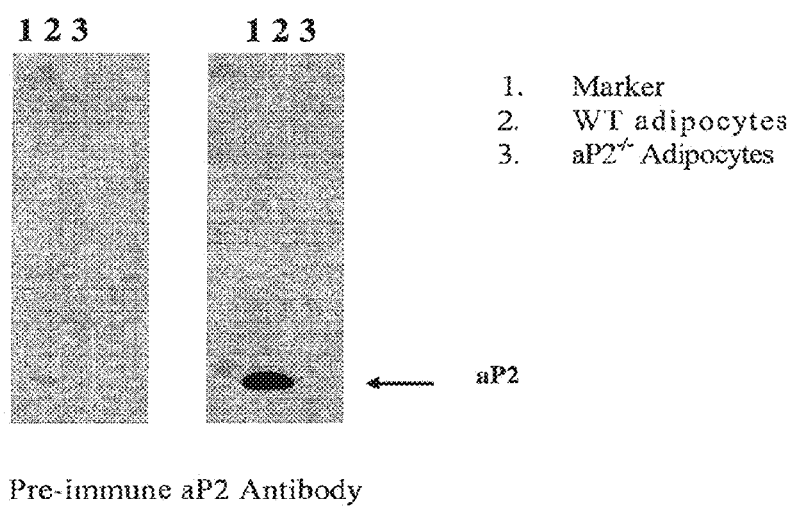
FIG. 9 is a series of immunoblots showing specificity of the aP2 antibody. Cell lysates from WT or aP2$^{-/-}$ adipocytes were resolved with SDS-PAGE and immunoblotted using purified pre-immune IgG or anti-aP2 IgG.
Figure 10A:
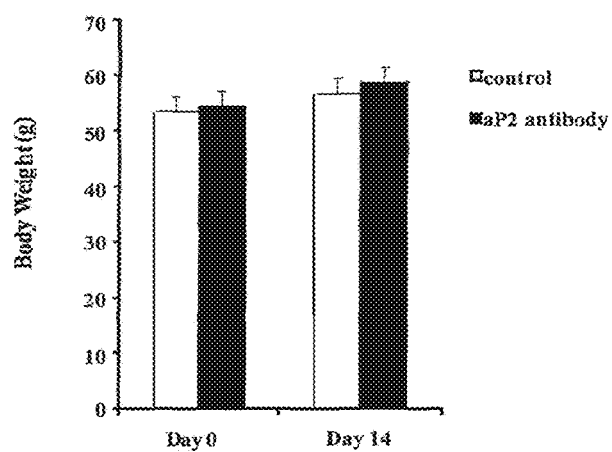
FIGS. 10A and 10B are bar graphs showing body weight (FIG. 10A) and serum free fatty acids (FIG. 10B) of mice treated with aP2 antibody. Body weights of mice treated with pre-immune (control) or aP2 antibody were recorded on day 0 and day 14 of antibody administration. Sera were collected from mice injected with or anti-aP2 antibody on day 0 and day 14 of antibody administration. Serum non-esterified fatty acids were determined using a commercial kit (Wako Chemicals USA, Inc.)
Figure 10B:
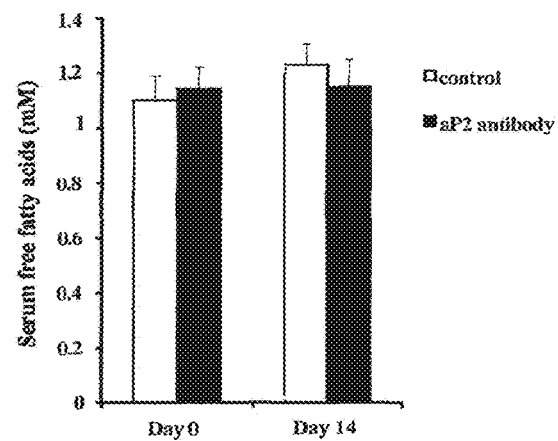

Elevated levels of lipolysis during obesity release excess fatty acids into serum. These fatty acids cause insulin resistance and increase liver glucose production by activating the gluconeogenic program. Therefore, circulating aP2 represents a target for mediating this effect. The beneficial effects of FABP-deficiency on metabolic regulation could be mediated, at least in part, by the loss-of-function of aP2 in serum, as its levels are significantly elevated in obesity. To investigate this hypothesis, a neutralizing antibody was developed to reduce serum aP2. The antibody specifically detected aP2 with very high sensitivity (FIG. 9). This antibody was injected into obese mice fed with high-fat diet, and the results confirmed that the aP2 antibody efficiently and rapidly depleted serum aP2 to the levels seen in lean controls without altering aP2 levels in adipose tissue (FIG. 6A). Antibody administration did not alter the body weight or serum free fatty acid levels of these mice (FIGS. 10A and 10B), but caused a significant decrease in blood glucose levels within two weeks of treatment (FIG. 6B). In a glucose tolerance test, mice receiving the aP2 antibody exhibited markedly improved glucose disposal curves compared to control animals (FIG. 6C). The obese mice with decreased serum aP2 also exhibited enhanced systemic insulin response as determined by insulin tolerance tests (FIG. 6D). These results indicated that elevated serum aP2 represents a required component for obesity-induced insulin resistance and glucose intolerance, and that suppressing circulating aP2 is useful as a method to block the metabolic deterioration associated with obesity.

Figure 6F:
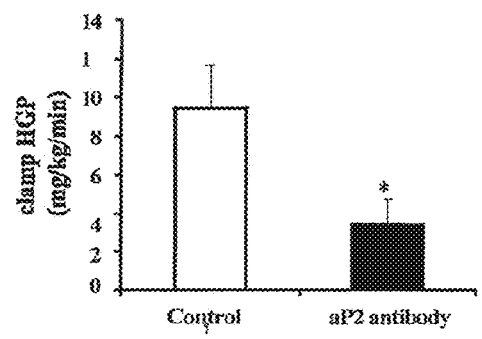
FIG. 6F is a bar graph showing clamp hepatic glucose production rate (cHGP) in mice on high-fat diet injected with pre-immune (Control) or aP2 antibody during hyperinsulinemic-euglycemic clamp study. *, $p<0.05$.
Figure 6G:
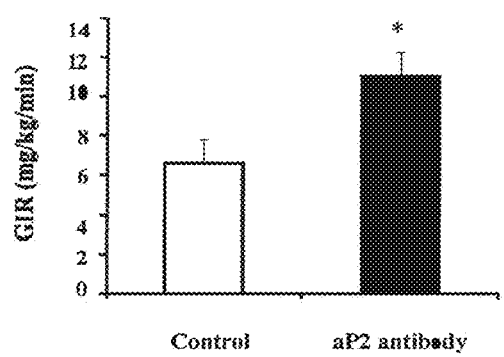
FIG. 6G is bar graph showing glucose infusion rate (GIR) in mice on high-fat diet injected with pre-immune (Control) or aP2 antibodies during hyperinsulinemic-euglycemic clamp study. *, $p<0.05$.
Figure 6H:
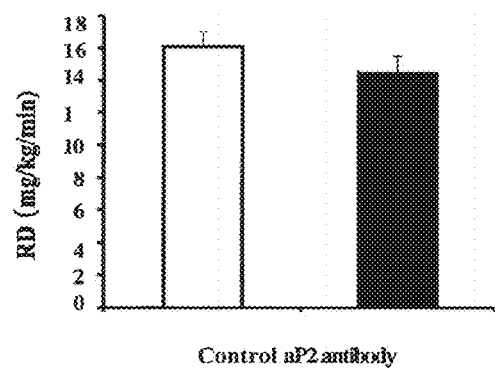
FIG. 6H is a bar graph showing whole body glucose metabolism (RD) in mice on high-fat diet injected with pre-immune (Control) or aP2 antibody during hyperinsulinemic-euglycemic clamp study.

Total body glucose flux and tissue-specific effects of antibody-mediated aP2 depletion was examined by using hyperinsulinemic-euglycemic clamp studies in mice treated with aP2 antibody or vehicle. Reduction of serum aP2 in obese mice resulted in significantly decreased basal and clamp hepatic glucose production (FIGS. 6E and 6F) indicating that liver is the primary target of circulating aP2 in regulating glucose metabolism. During the clamp studies, obese mice injected with the antibody required a significantly increased glucose infusion rates to maintain euglycemia, but exhibited no changes in their rate of glucose metabolism compared to controls (FIGS. 6G and 6H). These results indicate that the elevated glucose infusion rate in these animals is driven mainly by decreased hepatic glucose production. These data are in line with what has been observed in the whole body FABP knockout, which was also characterized by significantly decreased hepatic glucose production in both genetic and dietary obesity. Therefore, the effects of aP2 on hepatic glucose metabolism are primarily mediated by the secreted form of this protein.

Circulating aP2 Regulates Liver Glucose Production

Figure 6I:
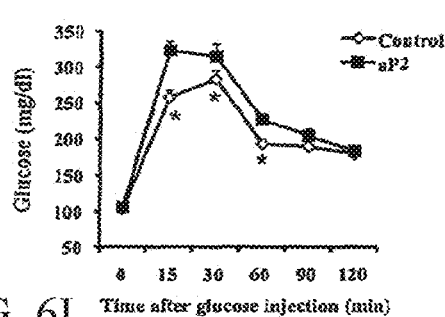
FIG. 6I is a line graph showing glucose tolerance test of mice on regular diet injected with control Gus protein or recombinant aP2 for two weeks. *, $p<0.05$.
Figure 6J:
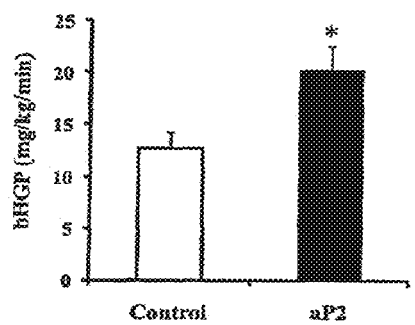
FIG. 6J is a bar graph showing basal hepatic glucose production rate (bHGP) in aP2-mal 1$^{-/-}$ mice that were infused with control Gus protein or recombinant aP2 during hyperinsulinemic-euglycemic clamp study. *, $p<0.05$.
Figure 6K:
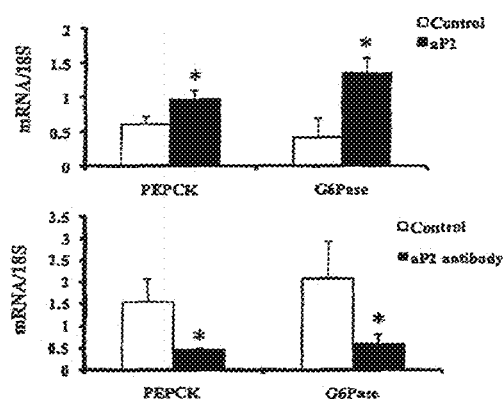
FIG. 6K is a bar graph showing gene expression in livers of WT mice infused with control protein or recombinant aP2 (top panel) or mice on HFD injected with control or aP2 antibody (bottom panel). PEPCK and G6P in liver tissues were analyzed with quantitative real-time PCR. *, $p<0.05$. These figures demonstrate regulation of systemic glucose homeostasis by serum aP2.
Figure 11:
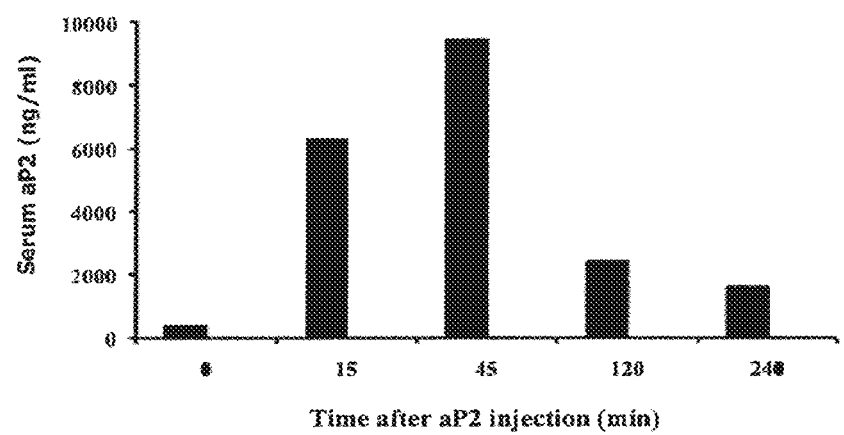
FIG. 11 is a bar graph showing serum aP2 in WT mice after recombinant aP2 injection. Serum samples of mice were collected at indicated time points after aP2 injection and aP2 levels were determined with an aP2 ELISA.
Figure 12A:
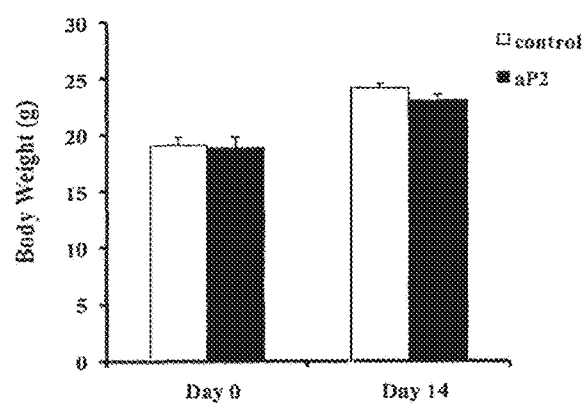
FIGS. 12A and 12B are bar graphs showing body weight (FIG. 12A) and serum free fatty acids (FIG. 12B) of mice injected with recombinant aP2. Body weights of mice injected with control or recombinant aP2 protein were recorded on day 0 and day 14 of protein administration. Sera were collected from mice injected with control or recombinant aP2 protein was recorded on day 0 and day 14 of protein administration. Serum non-esterified fatty acids were determined using a commercial kit (Wako Chemicals USA, Inc.)
Figure 12B:
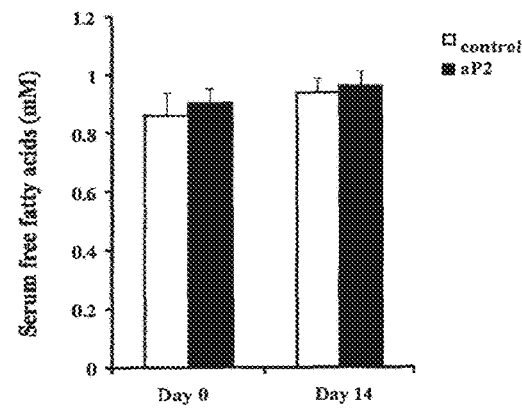
Figure 13:
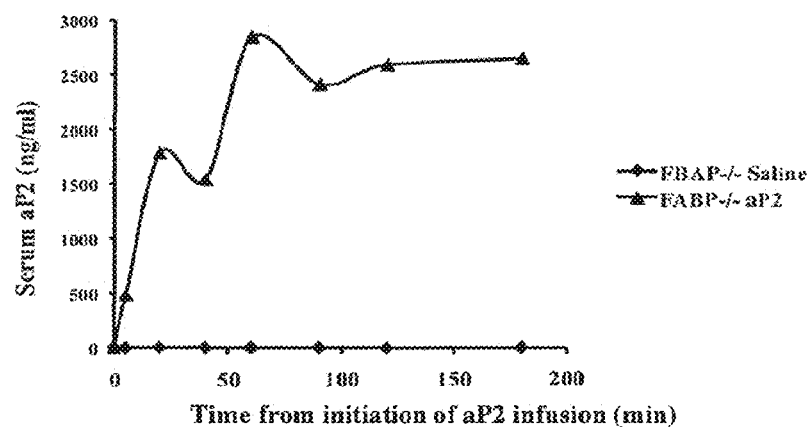
FIG. 13 is a line graph showing Serum aP2 in FABP-deficient (DKO) mice during aP2 infusion. Serum samples were collected from FABP-deficient mice during aP2 infusion at indicated time points. Serum aP2 levels were determined with an aP2 ELISA.

To directly address whether elevated serum aP2 has a negative impact on glucose metabolism, a condition of elevated serum aP2 in otherwise metabolically normal mice was created. Recombinant aP2 was injected into mice fed with a regular chow diet. Administration of a single dose of recombinant aP2 into mice led to increased levels of serum aP2 that lasted for several hours (FIG. 11). Recombinant aP2 was injected twice daily to ensure that mice maintained elevated aP2 in circulation during the majority of each 24-hour time period. Administration of recombinant aP2 did not alter the body weight or serum free fatty acid levels of mice during this period (FIGS. 12A and 12B). The lean healthy animals, however, exhibited mild glucose intolerance after receiving recombinant aP2 for two weeks as determined by a glucose tolerance test (FIG. 6I). This observation indicated that serum aP2 regulates glucose metabolism and increased serum aP2 alone can cause impaired glucose metabolism, even in the absence of any dietary contribution and alterations in body weight. Recombinant aP2 was infused into conscious FABP-deficient mice and examined the acute effects of serum aP2 on glucose metabolism with a hyperinsulinemic-euglycemic clamp. In this setting, aP2 infusion caused a rapid increase in serum aP2 levels in mice and established high steady-state serum levels after one hour which lasted until the end of the experiment (FIG. 13). During the clamp study, mice receiving aP2 displayed significantly increased basal hepatic glucose production (bHGP) (FIG. 6J). This is a profound effect considering that these mice had only received an aP2 infusion for 4 hours at the time the hepatic glucose production was examined. These findings and the absence of alterations in glucose metabolism rates further support the hypothesis that the liver is the primary target of serum aP2. The expression of genes regulating hepatic glucose production was examined in both aP2 infusion and depletion experiments. The two key genes in the gluconeogenesis pathway, phosphoenolpyruvate carboxykinase (PEPCK) and glucose-6-phosphatase (G6P), were both significantly upregulated in mice that had been infused with aP2 as compared to control (FIG. 6K Top panel). Conversely, mice receiving the aP2 antibody displayed dramatic decreases in these gluconeogenic genes (FIG. 6K bottom panel). These data indicate that serum aP2 regulates gluconeogenesis in the liver and the elevated levels of serum aP2 in obesity contribute to the increased hepatic glucose production often observed under diabetic conditions.

Exosome-Associated aP2 Secretion In Vitro and In Vivo

Figure 7A:
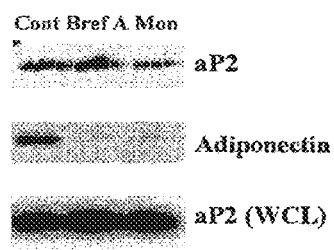
FIG. 7A is a photograph of an electrophonetic gel showing non-classical secretion of aP2. Conditioned medium from adipocytes treated with control, brefeldin A (Bref A) or monensin (Mon) were blotted using anti-aP2 or adiponectin antibodies. Whole cell lysate (WCL) was also blotted using anti-aP2 antibody.

To better understand how aP2 secretion is linked to and regulated by lipolysis, the molecular mechanism of aP2 secretion was examined. First, differentiated adipocytes were treated with inhibitors of classical secretory pathways and examined secreted proteins in the conditioned medium. While both brefeldin A and monensin treatment efficiently blocked adiponectin secretion, neither had any inhibitory effect on aP2 release (FIG. 7A), indicating that aP2 is secreted via a non-classical pathway. This finding is consistent with the fact that aP2 lacks a signal peptide sequence.

Figure 7B:
FIG. 7B is a photograph of an electrophonetic gel showing localization of aP2 to exosomes. Whole cell lysate (WCL), conditioned medium (CM) and exosome fractions (Exo) from differentiated adipocytes were blotted using anti-aP2 or MFG-E8 antibodies.

One of a variety of mechanisms previously described for non-classical secretion is the exosome-dependent pathway. To determine whether aP2 secretion utilizes this pathway, exosomes were isolated from adipocyte conditioned medium; the presence of aP2 was examined in these fractions. aP2 was enriched and readily detectable in the exosomal fraction, in a manner similar to milk fat globule-EGF factor 8 (MFG-E8), an established exosome marker (FIG. 7B), indicating that aP2 is indeed secreted via exosomes in adipocytes.

Figure 7C:
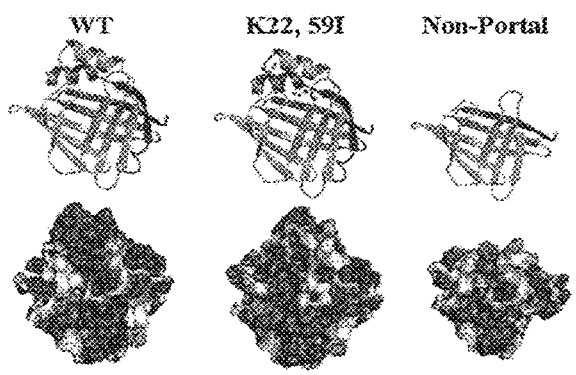
FIG. 7C is a series of diagrams showing structure and surface charges of WT and mutant aP2. Top panel: 3D structure of WT and two aP2 mutants, bottom panel: electrostatic potential of WT and two aP2 mutants. These renderings were prepared with PyMol http://pymol.sourceforge.net/) and WT aP2 were based on previously described 3-D structure (PDB ID: 1LIE).
Figure 7D:
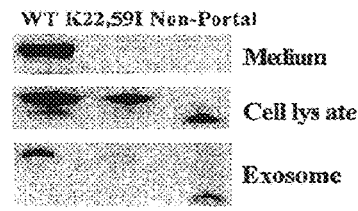
FIG. 7D is a photograph of an electrophonetic gel showing whole cell lysate (WCL), exosome fraction and immunoprecipitated conditioned medium from HEK 293 cells transfected with WT or mutant aP2 were blotted using anti-flag antibody.

Regulated Exosomal Secretion of an Adipose Tissue Lipid Chaperone Links Lipolysis to Hepatic Glucose Production Membrane targeting is a key step for exosome-mediated secretion. While the majority of aP2 is localized in the cytosol, aP2 has been found to transiently interact with phospholipid membranes. The 3D structure of aP2 is composed of a 10-stranded β-barrel with two top α helices serving as the portal for fatty acid entry[25] (FIG. 7C, left panel). Two components of the aP2 protein have been proposed to contribute to its membrane association: (1) a ridge of strong positive surface potentials, contributed by the lysine residues, that mediates an electrostatic interaction with the negatively charged phospholipids and (2), the portal region that directly interacts with the membrane. To explore the mechanisms that might underlie aP2's translocation into the exosome, aP2 mutants were created with the two critical surface residues, lysine 22 and 59, changed to isoleucine, (FIG. 7C, middle panel) or with complete deletion of the portal region (FIG. 7C, right panel). These mutations did not alter the overall folding of aP2 but both blocked aP2's secretion from the cells (FIG. 7D), indicating that aP2's association with the phospholipid membrane is an absolute requirement for its secretion. The aP2 mutants described above, which lost secretory capacity, also had dramatically reduced exosome localization (FIG. 7D), indicating that exosome-targeting is an essential step for aP2 secretion.

Having observed the induction of aP2 secretion by lipolysis, aP2 translocation into the exosomes was examined during either lipolysis or exposure to fatty acids. Under both conditions, a clear enrichment of aP2 in exosomes (FIG. 7E) was seen, suggesting that increased aP2 targeting to exosomes during lipolysis results in its elevated secretion. Exosome-like microvesicles have been identified in blood, but hematopoietic cells have usually been considered to be the source of these vesicles. To investigate whether aP2—associated exosomes also exist in circulation, the exosome fraction from plasma of mice was isolated and blotted for aP2. The aP2-associated exosomes exist in circulation of WT but not aP2 knockout mice (FIG. 7F), suggesting that adipocytes might secrete exosomes to communicate with other organs. Results showed significantly increased aP2 levels in the circulating exosomes of obese mice, indicating the aP2—associated exosomes might be implicated in obesity-induced metabolic dysregulation (FIG. 7F).

These data provide evidence that aP2 is a novel adipokine which is regulated by nutritional status and obesity. In adipocytes, aP2 secretion is activated by lipids and lipolysis and mediated by an exosome-associated secretory pathway (FIG. 7G). In mice, serum aP2 is entirely derived from adipocytes with a marked increase in dietary or genetic obesity models as well as in vivo lipolysis. Depletion of serum aP2 in obese mice suppresses the elevated hepatic glucose production, while the converse—increasing serum aP2 in lean mice—led to enhanced hepatic glucose production. These results indicate that secreted aP2 is a key component of the adipo-hepatic communication system linking lipolysis to liver glucose production (FIG. 7G).

Serum free fatty acids represent a key energy source during fasting, but it is also recognized that elevated lipolysis and serum fatty acids are linked to dysregulation of systemic glucose homeostasis and represent one of the critical underlying causes of obesity-induced metabolic disorders. Excess fatty acids cause insulin resistance in muscle and liver by reducing glucose utilization and attenuating insulin-mediated suppression of glucose production, respectively. Utilizing the well-controlled hormonal conditions of a pancreatic clamp, fatty acids have also been shown to directly increase liver glucose production independent of insulin or glucagon action. This effect has been attributed to the activation of gluconeogenesis pathways by fatty acids. Some mouse models and conditions, have been shown to uncouple liver glucose production from increased serum fatty acids, which suggests that other factors are required to link lipolysis and fatty acids to hepatic gluconeogenesis. The findings presented herein identify aP2 as a secreted adipocyte protein and one of these factors.

Identification of aP2 as an adipokine offers several insights into the endocrine functions of adipose tissue. This protein is unique in its ability to directly bind lipids and to be secreted in response to lipolysis. Thus, it serves as a sensor of the lipid status of adipose tissue or as a signal to other metabolic organs in response to metabolic regulation or dietary changes. Additionally, lipolysis-stimulated, exosome-associated aP2 secretion might help explain how adipocytes sustain a dramatic secretory capacity despite the massive volume of lipid droplets and the limitations imposed on the endoplasmic reticulum. aP2, when activated by fatty acids, translocates to lipid droplets or lipid bodies. Lipid bodies function as a membrane-trafficking organelles, and certain lipid body resident proteins, such as perilipin A, were identified to be secreted via exosomes. It is possible then, that the mechanism of aP2 secretion allows the adipocyte to meet the demands of efficiently delivering lipids and proteins outside the cell (FIG. 7G).

The tight coupling of aP2 secretion and serum levels to adipose lipolysis indicates that aP2 represents a novel part of the physiological and/or pathophysiological consequences of the lipolytic response. aP2's apparent requirement as a serum component for fatty acids to fully activate liver gluconeogenesis argues that obesity-induced hyper-aP2-emia might underlie the elevated hepatic glucose production that is the hallmark of hyperglycemia in subjects with type 2 diabetes.

Evidence points to the central role of aP2 in metabolic disease not only in experimental models but in humans as well. While the therapeutic value of aP2 inhibition is a clinical goal, its chemical targeting in tissue has been a challenge. The data described herein demonstrate that when increased serum aP2 levels associated with obesity are normalized using a neutralizing antibody, glucose metabolism is greatly enhanced without any alteration in adipose tissue aP2 levels. Serum aP2 levels is associated with metabolic disease risk in humans and fasting, circulating aP2 is more strongly related to metabolic risk than increased fasting free fatty acids. Administration of compositions to neutralize serum aP2 is an efficient approach to treat metabolic disorders, especially type 2 diabetes.

Other embodiments are within the following claims.

What is claimed:

1. A method of treating diabetes in a human in need thereof comprising administering to the human an effective amount of an Adipocyte Protein 2 (aP2)-specific antibody that specifically binds to aP2 in blood or serum, wherein administration of the aP2-specific antibody results in reduced serum aP2 activity or reduced blood glucose levels.

2. The method of claim 1, wherein administration of the aP2-specific antibody results in reduced glucose production.

3. The method of claim 1, wherein the aP2-specific antibody is a monoclonal antibody.

4. The method of claim 1, wherein the aP2-specific antibody is a polyclonal antibody.

5. The method of claim 1, wherein the human has Type II diabetes.

* * * * *

SEQUENCE LISTING

```
<160> NUMBER OF SEQ ID NOS: 8

<210> SEQ ID NO 1
<211> LENGTH: 614
<212> TYPE: DNA
<213> ORGANISM: Mus musculus

<400> SEQUENCE: 1
cctttctcac ctggaagaca gctcctcctc gaaggtttac aaaatgtgtg atgcctttgt      60
gggaacctgg aagcttgtct ccagtgaaaa cttcgatgat tacatgaaag aagtgggagt     120
gggctttgcc acaaggaaag tggcaggcat ggccaagccc aacatgatca tcagcgtaaa     180 tgggatttg gtcaccatcc ggtcagagag tacttttaaa aacaccgaga tttccttcaa     240
actgggcgtg gaattcgatg aaatcaccgc agacgacagg aaggtgaaga gcatcataac     300
cctagatggc ggggccctgg tgcaggtgca gaagtgggat ggaaagtcga ccacaataaa     360
gagaaaacga gatggtgaca agctggtggt ggaatgtgtt atgaaaggcg tgacttccac     420
aagagtttat gaaagggcat gagccaaagg aagaggcctg gatggaaatt tgcatcaaac     480
actacaatag tcagtcggat ttattgtttt ttttaaagat atgattttcc actaataagc     540
aagcaattaa tttttttctga agatgcattt tattggatat ggttatgttg attaaataaa    600
acctttttag actt                                                      614

<210> SEQ ID NO 2
<211> LENGTH: 634
<212> TYPE: DNA
<213> ORGANISM: homo sapiens

<400> SEQUENCE: 2
ggaattccag gagggtgcag cttccttctc accttgaaga ataatcctag aaaactcaca      60
aaatgtgtga tgcttttgta ggtacctgga aacttgtctc cagtgaaaac tttgatgatt     120
atatgaaaga agtaggagtg ggctttgcca ccaggaaagt ggctggcatg gccaaaccta     180
acatgatcat cagtgtgaat gggatgtga tcaccattaa atctgaaagt acctttaaaa     240
atactgagat ttccttcata ctgggccagg aatttgacga agtcactgca gatgacagga     300
aagtcaagag caccataacc ttagatgggg gtgtcctggt acatgtgcag aaatgggatg     360
gaaaatcaac caccataaag agaaaacgag aggatgataa actggtggtg gaatgcgtca     420
tgaaaggcgt cacttccacg agagtttatg agagagcata agccaaggga cgttgacctg     480
```

```
gactgaagtt cgcattgaac tctacaacat tctgtgggat atattgttca aaaagatatt    540
gttgttttcc ctgatttagc aagcaagtaa ttttctccca agctgatttt attcaatatg    600
gttacgttgg ttaaataact tttttagat ttag                                 634
```

```
<210> SEQ ID NO 3
<211> LENGTH: 132
<212> TYPE: PRT
<213> ORGANISM: homo sapiens

<400> SEQUENCE: 3

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
                20                  25                  30

Val Ala Gly Met Ala Lys Pro Asn Met Ile Ile Ser Val Asn Gly Asp
            35                  40                  45

Val Ile Thr Ile Lys Ser Glu Ser Thr Phe Lys Asn Thr Glu Ile Ser
        50                  55                  60

Phe Ile Leu Gly Gln Glu Phe Asp Glu Val Thr Ala Asp Asp Arg Lys
65                  70                  75                  80

Val Lys Ser Thr Ile Thr Leu Asp Gly Gly Val Leu Val His Val Gln
                85                  90                  95

Lys Trp Asp Gly Lys Ser Thr Thr Ile Lys Arg Lys Arg Glu Asp Asp
            100                 105                 110

Lys Leu Val Val Glu Cys Val Met Lys Gly Val Thr Ser Thr Arg Val
        115                 120                 125

Tyr Glu Arg Ala
    130

<210> SEQ ID NO 4
<211> LENGTH: 132
<212> TYPE: PRT
<213> ORGANISM: Mus musculus

<400> SEQUENCE: 4

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
                20                  25                  30

Val Ala Gly Met Ala Lys Pro Asn Met Ile Ile Ser Val Asn Gly Asp
            35                  40                  45

Leu Val Thr Ile Arg Ser Glu Ser Thr Phe Lys Asn Thr Glu Ile Ser
        50                  55                  60

Phe Lys Leu Gly Val Glu Phe Asp Glu Ile Thr Ala Asp Asp Arg Lys
65                  70                  75                  80

Val Lys Ser Ile Ile Thr Leu Asp Gly Gly Ala Leu Val Gln Val Gln
                85                  90                  95

Lys Trp Asp Gly Lys Ser Thr Thr Ile Lys Arg Lys Arg Asp Gly Asp
            100                 105                 110

Lys Leu Val Val Glu Cys Val Met Lys Gly Val Thr Ser Thr Arg Val
        115                 120                 125

Tyr Glu Arg Ala
    130

<210> SEQ ID NO 5
```

```
<211> LENGTH: 21
<212> TYPE: DNA
<213> ORGANISM: Artificial sequence
<220> FEATURE:
<223> OTHER INFORMATION: Chemically synthesized primer

<400> SEQUENCE: 5
ctgcataacg gtctggactt c                                              21

<210> SEQ ID NO 6
<211> LENGTH: 19
<212> TYPE: DNA
<213> ORGANISM: Artificial sequence
<220> FEATURE:
<223> OTHER INFORMATION: Chemically synthesized primer

<400> SEQUENCE: 6
cagcaactgc ccgtactcc                                                 19

<210> SEQ ID NO 7
<211> LENGTH: 21
<212> TYPE: DNA
<213> ORGANISM: Artificial sequence
<220> FEATURE:
<223> OTHER INFORMATION: Chemically synthesized primer

<400> SEQUENCE: 7
cgactcgcta tctccaagtg a                                              21

<210> SEQ ID NO 8
<211> LENGTH: 20
<212> TYPE: DNA
<213> ORGANISM: Artificial sequence
<220> FEATURE:
<223> OTHER INFORMATION: Chemically synthesized primer

<400> SEQUENCE: 8
gttgaaccag tctccgacca                                                20
```